(12) United States Patent
Hayami et al.

(10) Patent No.: US 11,564,560 B2
(45) Date of Patent: Jan. 31, 2023

(54) IMAGE PROCESSING APPARATUS, OPERATING METHOD OF IMAGE PROCESSING APPARATUS, AND COMPUTER-READABLE RECORDING MEDIUM

(71) Applicant: OLYMPUS CORPORATION, Tokyo (JP)

(72) Inventors: Takehito Hayami, Hachioji (JP); Yamato Kanda, Hino (JP); Takashi Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 680 days.

(21) Appl. No.: 16/662,373

(22) Filed: Oct. 24, 2019

(65) Prior Publication Data

US 2020/0054400 A1 Feb. 20, 2020

Related U.S. Application Data

(63) Continuation of application No. PCT/JP2017/016637, filed on Apr. 26, 2017.

(51) Int. Cl.
*A61K 35/12* (2015.01)
*G06K 9/00* (2022.01)
(Continued)

(52) U.S. Cl.
CPC .......... *A61B 1/045* (2013.01); *A61B 1/00045* (2013.01); *A61B 1/000094* (2022.02);
(Continued)

(58) Field of Classification Search
CPC ........ G06K 9/00; A61B 17/083; A61B 1/043; A61K 35/12
(Continued)

(56) References Cited

U.S. PATENT DOCUMENTS

2012/0188351 A1\* 7/2012 Kaku ...................... G06T 7/136
348/E7.085
2013/0329027 A1 12/2013 Igarashi
(Continued)

FOREIGN PATENT DOCUMENTS

JP 2006-187385 A 7/2006
JP 2006-304995 A 11/2006
(Continued)

OTHER PUBLICATIONS

International Search Report dated Jul. 18, 2017 issued in PCT/JP2017/016637.
(Continued)

*Primary Examiner* — Seyed H Azarian
(74) *Attorney, Agent, or Firm* — Scully, Scott, Murphy & Presser, P.C.

(57) ABSTRACT

An image processing apparatus includes a processor including hardware, the processor being configured to: estimate, based on image information from a medical device that includes at least an endoscope, a plurality of procedure actions of an operator of the endoscope; perform different supports respectively for procedures by the operator, according to an estimation result of the procedure actions; and output a display for the supports to a display.

18 Claims, 23 Drawing Sheets

(51) Int. Cl.
*A61B 1/045* (2006.01)
*A61B 34/00* (2016.01)
*G06T 7/50* (2017.01)
*G06T 7/70* (2017.01)
*A61B 1/00* (2006.01)
*A61B 1/018* (2006.01)
*G06T 7/00* (2017.01)
*G06V 10/10* (2022.01)
*A61B 34/10* (2016.01)
*A61B 34/20* (2016.01)
*A61B 5/00* (2006.01)
*A61B 17/29* (2006.01)
*A61B 17/32* (2006.01)
*A61B 17/00* (2006.01)
*A61B 17/12* (2006.01)
*A61B 18/14* (2006.01)
*A61M 25/00* (2006.01)

(52) U.S. Cl.
CPC .............. *A61B 1/018* (2013.01); *A61B 34/25* (2016.02); *G06T 7/0012* (2013.01); *G06T 7/50* (2017.01); *G06T 7/70* (2017.01); *G06V 10/10* (2022.01); *A61B 5/489* (2013.01); *A61B 17/29* (2013.01); *A61B 17/320068* (2013.01); *A61B 2017/00358* (2013.01); *A61B 2017/12004* (2013.01); *A61B 2018/1412* (2013.01); *A61B 2034/107* (2016.02); *A61B 2034/2057* (2016.02); *A61B 2034/2065* (2016.02); *A61B 2034/254* (2016.02); *A61M 25/0084* (2013.01); *G06T 2207/10068* (2013.01); *G06T 2207/30096* (2013.01); *G06T 2207/30101* (2013.01); *G06V 2201/034* (2022.01)

(58) Field of Classification Search
USPC ........ 382/100, 103, 106, 128–133, 153–154, 382/162, 173–174, 181, 199, 209, 219, 382/224, 254, 274, 285–291, 305, 317; 600/476, 486; 606/3; 607/88; 378/4, 378/21; 348/7.085
See application file for complete search history.

(56) References Cited

U.S. PATENT DOCUMENTS

| 2014/0024948 A1* | 1/2014 | Shida ................ A61B 1/00009 600/476 |
| 2014/0031838 A1* | 1/2014 | Namiki ................ A61B 34/37 606/130 |
| 2014/0213871 A1 | 7/2014 | Watanabe |
| 2015/0105758 A1* | 4/2015 | Igarashi ............... A61B 1/0638 606/3 |
| 2015/0105769 A1* | 4/2015 | Igarashi ............... A61B 17/122 607/88 |
| 2018/0353244 A1* | 12/2018 | Kashima ............... G06T 11/203 |

FOREIGN PATENT DOCUMENTS

| JP | 2007-244518 A | 9/2007 |
| JP | 2012-152266 A | 8/2012 |
| JP | 2016-158752 A | 9/2016 |
| JP | 2016-158886 A | 9/2016 |
| WO | WO 2012/132790 A1 | 10/2012 |
| WO | WO 2013/051431 A1 | 4/2013 |
| WO | WO 2013/145408 A1 | 10/2013 |
| WO | WO 2016/185912 A1 | 11/2016 |

OTHER PUBLICATIONS

Okamoto, Takayuki et al., "Real time detection of bleeding region for building a hemostasis support system in laparoscopic surgery", The Institute of Electronics, Information and Communication Engineers Technical Report (Jan. 19, 2016), vol. 115, No. 401, pp. 157-160, with English Abstract.
CG-Arts Society, Digital Image Processing [revised new edition], Mar. 9, 2015, 18 pages, together with partial English translation.

* cited by examiner

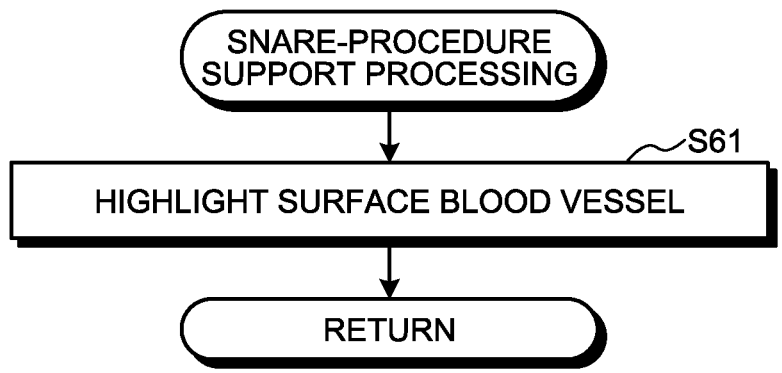
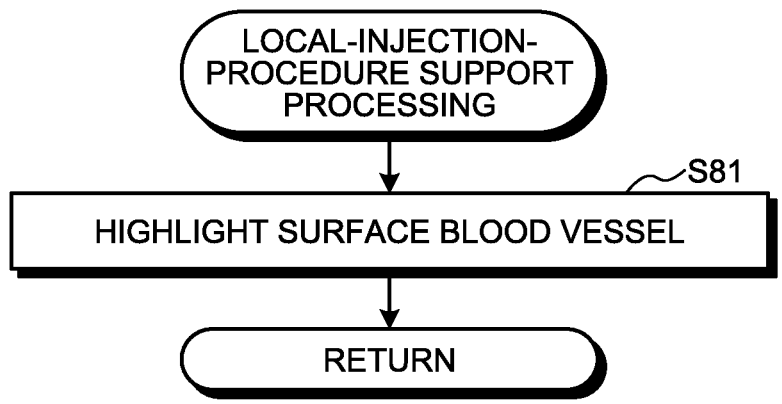

IMAGE PROCESSING APPARATUS, OPERATING METHOD OF IMAGE PROCESSING APPARATUS, AND COMPUTER-READABLE RECORDING MEDIUM

CROSS-REFERENCE TO RELATED APPLICATION

This application is a continuation of International Application No. PCT/JP2017/016637, filed on Apr. 26, 2017, the entire contents of which are incorporated herein by reference.

BACKGROUND

1. Technical Field

The present disclosure relates to an image processing apparatus, an operating method of an image processing apparatus, and a computer-readable recording medium for supporting an action of an operator that operates a medical device, based on information from a medical device equipped with an imaging device that is inserted into a lumen of a living body, and that captures chronologically successive images.

2. Related Art

JP-A-2016-158752 discloses a technique of identifying a kind of treatment tool from an observation image in which an inside of the body of a patient is imaged when a treatment tool is being used in endoscopy, and of acquiring an examination image of the same patient and of an examination in which the same type of treatment tool is used, from among plural examination images recorded in an image management system based on the identified type of treatment tool and patient identification information of the patient. In this technique, the examination image acquired from the image management system and the observation image captured by an endoscope are displayed at the same time on a display device, thereby supporting endoscopy.

SUMMARY

In some embodiments, an image processing apparatus includes a processor including hardware, the processor being configured to: estimate, based on image information from a medical device that includes at least an endoscope, a plurality of procedure actions of an operator of the endoscope; perform different supports respectively for procedures by the operator, according to an estimation result of the procedure actions; and output a display for the supports to a display.

In some embodiments, an operating method of an image processing apparatus includes: estimating, based on image information from a medical device that includes at least an endoscope, a plurality of procedure actions of an operator of the endoscope; performing different supports respectively for the procedures by the operator, according to an estimation result at the estimating; and outputting a supporting display at the supporting to a display.

In some embodiments, provided is a non-transitory computer-readable recording medium with an executable program stored thereon. The program causes a computer to perform: estimating, based on image information from a medical device that includes at least an endoscope, a plurality of procedure actions of an operator of the endoscope; performing different supports respectively for the procedures by the operator, according to an estimation result at the estimating; and outputting a supporting display at the supporting to a display.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is a flowchart illustrating an overview of snare-procedure support processing in FIG. 3;

FIG. 7 is a flowchart illustrating an overview of local-injection-procedure support processing in FIG. 3;

DETAILED DESCRIPTION

Hereinafter, an image processing apparatus, an image processing method, and a program used for medical endoscope system will be described as forms (hereinafter, "embodiments") to implement the disclosure. In the following, an example, an apparatus that estimates actions in a procedure of an operator (surgical operator) based on chronologically-aligned intraluminal images (hereinafter, "endoscopic images") of a living body in which an inside of a lumen of a subject are successively imaged by an endoscope including a flexible endoscope, a rigid endoscope, and the like, or a capsule endoscope (hereinafter, collectively referred to as "medical device" simply), or based on information from the medical device, and that supports the procedure by the operator according to the estimation result will be described. The procedure includes a procedure on the subject, a procedure after lesion diagnosis, or a procedure at least one of marking, extraction, peeling, cut, resection, holding, incision, hemostasis, ablation, puncturing, and local injection of saline or drug (for example, sodium hyaluronate in which a coloring matter of blue is mixed) of a pathogenic region after a lesion is found or after a lesion is confirmed, and the like, and further includes a combination thereof. Moreover, the endoscopic image is a color image usually having pixel levels (pixel values) corresponding to wavelength components of R (red), G (green), B (blue) at respective pixel positions. A lesion region is a specific region in which a part considered as lesion or abnormality, such as bleeding, reddening, coagulated blood, a tumor, an erosion, an ulcer, an aphtha, and abnormal villi, is shown, that is, an abnormal region. Furthermore, the information from a medical device includes information about operation by an operator with respect to the medical device, a start signal to start a procedure with a treatment tool, such as an energy device, and the like in addition to the endoscopic images. Moreover, these embodiments are not intended to limit the disclosure. Furthermore, like reference symbols are assigned to like parts throughout the drawings.

First Embodiment

Configuration of Endoscope System

Figure 1:
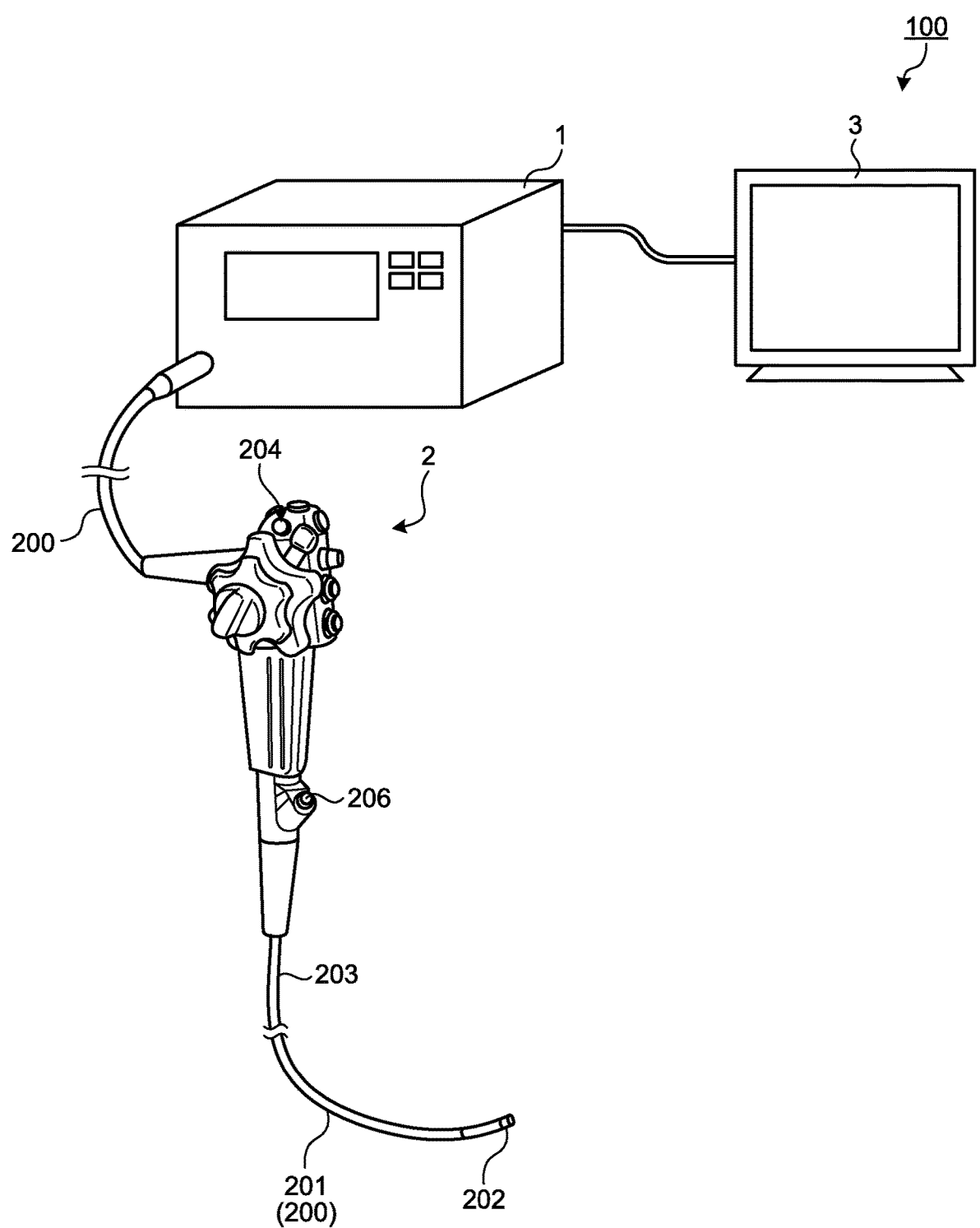
FIG. 1 is a schematic diagram illustrating a schematic configuration of an endoscope system according to a first embodiment of the disclosure.

FIG. 1 is a schematic diagram illustrating a schematic configuration of an endoscope system according to a first embodiment of the disclosure.

An endoscope system 100 illustrated in FIG. 1 includes an image processing apparatus 1 to which an endoscope 2 is detachably connected, and that performs predetermined image processing with respect to an endoscopic image (image signal) transmitted from the endoscope 2, and that supplies emission light to irradiate an inside of a subject, the flexible endoscope 2 that generates an endoscopic image by inserting a distal end portion into the body of the subject and by imaging an inside of the body of the subject, and a display device that displays the endoscopic image subjected to the image processing by the image processing apparatus 1. The image processing apparatus 1 and the endoscope 2 are electrically and optically connected with each other.

The image processing apparatus 1 subjects the endoscopic image transmitted through a transmission cable 200 to predetermined image processing, and outputs it to a display device 3. Moreover, the image processing apparatus 1 supplies, to the endoscope 2 through the transmission cable 200, illumination light to emit from a distal end portion 202 of the endoscope 2. The illumination light is light having a wavelength band of red, light having a wavelength band of green, and light having a wavelength band of blue in the case of sequential lighting, and is white light in the case of simultaneous lighting. Furthermore, the illumination light includes a special light (for example, light including 390 nanometers (nm) to 445 nm and 530 nm to 550 nm) to highlight blood vessels of a surface area of tissue, or special light (light including 790 nm to 820 nm and 905 nm to 970 nm) to highlight deep blood vessels of tissue. A detailed configuration of the image processing apparatus 1 will be described later.

The endoscope 2 images an inside of a body of the subject by inserting an insertion portion 201 that is a part of the transmission cable 200 into a lumen of the subject, and outputs an endoscopic image to the image processing apparatus 1. Moreover, the endoscope 2 includes an optical system (not shown) and an imaging device (not shown) provided at one end of the transmission cable 200, which is on a side of the distal end portion 202 of the insertion portion 201 inserted into a lumen of the subject, and includes an operation unit 204 that accepts various kinds of operations with respect to the endoscope 2 provided at a proximal end 203 of the insertion portion 201. An image signal acquired by the endoscope 2 is transmitted to the image processing apparatus 1 through the transmission cable 200 having, for example, a length of several meters (m). It is noted that even though the endoscope 2 according to the first embodiment is explained as a flexible endoscope in the following, it is not limited thereto. A rigid endoscope in which the insertion portion is rigid, or an optical endoscope in which a camera head is connected to an ocular unit of an optical endoscope, such as a fiberscope and an optical sinuscope may be applied. Furthermore, the endoscope 2 is not limited to one with the imaging device provided at the distal end portion 202 of the insertion portion 201, but may be, for example, a flexible endoscope that includes an imaging device provided at the proximal end 203 of the insertion portion 201, and that is capable of acquiring an optical image transmitted through an optical fiber from the distal end portion 202 to the proximal end 203 of the insertion portion 201. Furthermore, the endoscope 2 is configured such that a treatment tool is inserted into the body of the subject from the distal end portion 202 through a treatment tool channel 206 (forceps inlet) of the operation unit 204. A treatment tool may be, of course, inserted into the body of the subject without passing through the treatment tool channel 206 in the first embodiment.

The display device 3 displays an image corresponding to the image signal subjected to the image processing by the image processing apparatus 1. Moreover, the display device 3 displays various kinds of information relating to the endoscope system 100. The display device 3 is constituted of a display panel of liquid crystal or organic electroluminescence (EL), or the like.

Configuration of Image Processing Apparatus

Next, a configuration of the image processing apparatus 1 described above will be explained.

Figure 2:
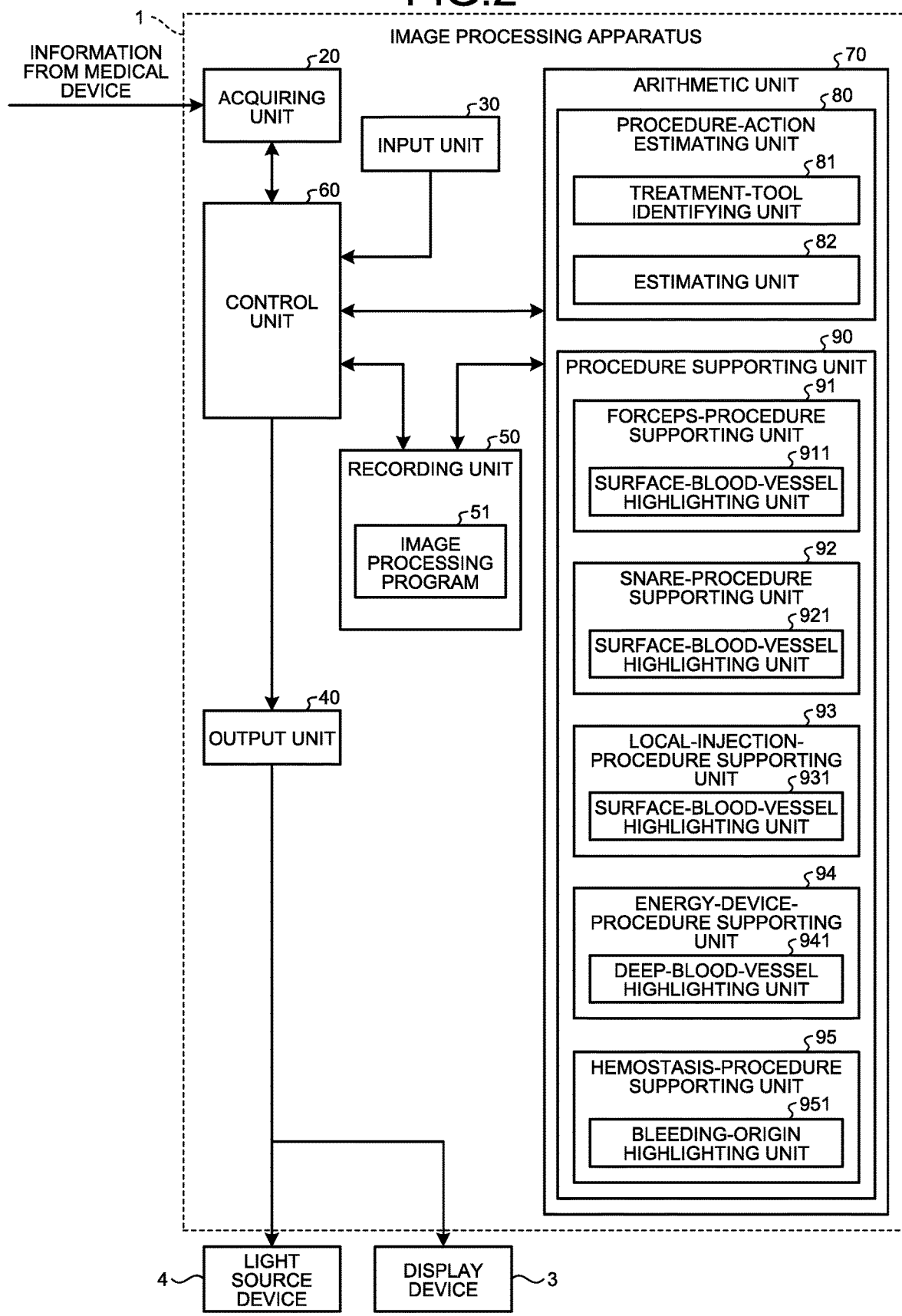
FIG. 2 is a block diagram illustrating a configuration of an image processing apparatus according to the first embodiment of the disclosure.

FIG. 2 is a block diagram illustrating the configuration of the image processing apparatus 1.

The image processing apparatus 1 illustrated in FIG. 2 includes an acquiring unit 20 that acquires information including an endoscopic image from a medical device or an external treatment tool, an input unit 30 that accepts an input signal that is input by an operation from outside, an output unit 40 that outputs an image or various kinds of information to the display device 3 or a light source device 4, a recording unit 50 that records the endoscopic image acquired by the acquiring unit 20, information from a medical device, information from a treatment tool, and various kinds of programs, a control unit 60 that controls entire operation of the image processing apparatus 1, and an arithmetic unit 70 that switches predetermined image processing with respect to an endoscopic image and processing of the light source device 4. In the first embodiment, the acquiring unit 20 is configured to acquire information including an endoscopic image from an external medical device, but the image processing apparatus 1 may be configured to include an imaging unit having an imaging function, to capture an endoscopic image of the subject.

The acquiring unit 20 is configured appropriately according to a mode of a system including a medical device. For example, when a portable recording medium is used for communication of an endoscopic image with the medical device, the acquiring unit 20 is configured as a reader device that reads an endoscopic image recorded therein, detachably mounting this recording medium. Moreover, when a server that records an endoscopic image imaged by the medical device is used, the acquiring unit 20 is configured with a communication device or the like that is capable of mutually communicating with this server, and acquires an endoscopic image through data communication with the server. Furthermore, the acquiring unit 20 may be configured with an interface device or the like to which an endoscopic image is input through a cable from the medical device.

The input unit 30 is implemented by, for example, an input device, such as a keyboard, a mouse, a touch panel, and various kinds of switches, and outputs an input signal accepted in response to an operation from outside, to the control unit 60. Note that the input unit 30 is not necessarily required to be arranged in wired connection, but may be arranged, for example, in wireless connection.

The output unit 40 outputs information extracted by calculation by the arithmetic unit 70, or an image to the display device 3 connected by wired connection, or to the display device 3 connected by wireless communication, and the like. Moreover, the output unit 40 outputs an instruction signal according to a result of calculation by the arithmetic unit 70, to the light source device 4. The output unit 40 may be constituted of a display panel of liquid crystal or organic EL, or the like, to display various kinds of images including an image subjected to image processing by calculation of the arithmetic unit 70, or to output an alarm by sound, characters, and the like.

The recording unit 50 is implemented by various kinds of integrated circuit (IC) memory, such as a flash memory, a read-only memory (ROM), and a random access memory (RAM), a hard disk equipped therein or connected through a data communication terminal, or the like. The recording unit 50 records a program to operate the image processing apparatus 1, data used during execution of this program, and the like in addition to endoscopic images and moving images acquired by the acquiring unit 20. For example, the recording unit 50 records an image processing program 51 to identify a kind of a treatment tool from an endoscopic image, and various kinds of information and template images used during execution of this program, and the like. Furthermore, the recording unit 50 records templates in which characteristics of lesions are defined in advance for lesion detection, bleeding detection, and the like performed by the arithmetic unit 70, criteria used to determine a lesion, criteria used for bleeding determination, templates for determination of a type of a treatment tool, and the like.

The control unit 60 is constituted of a general-purpose processor, such as a central processing unit (CPU), or a dedicated processor of various kinds of arithmetic circuits or the like, such as an application specific integrated circuit (ASIC) and a field programmable gate array (FPGA). When the control unit 60 is a general-purpose processor, the control unit 60 overall controls entire operation of the image processing apparatus 1 by reading various kinds of programs recorded in the recording unit 50, to send instructions to respective components constituting the image processing apparatus 1, to perform data transfer, and the like. Moreover, when the control unit 60 is a dedicated processor, the processor may perform various kinds of processing singly, or may perform various kinds of processing in cooperation with or conjointly with the recording unit 50, by using various kinds of data recorded in the recording unit 50.

The arithmetic unit 70 is constituted of a general-purpose processor, such as a CPU, or a dedicated processor of various kinds of arithmetic circuits or the like that perform specific functions, such as an ASIC and an FPGA. When the arithmetic unit 70 is a general-purpose processor, the arithmetic unit 70 reads the image processing program 51 from the recording unit 50, and thereby estimates actions in a procedure by an operator based on an acquired endoscopic image or information from the medical device, and supports the procedure by the operator according to this estimation result. Furthermore, when the arithmetic unit 70 is a dedicated processor, the processor may perform various kinds of processing singly, or may perform processing in cooperation with or conjointly with the recording unit 50 by using various kinds of data recorded in the recording unit 50.

Detailed Configuration of Arithmetic Unit

Next, a detailed configuration of the arithmetic unit 70 will be described. The arithmetic unit 70 includes a procedure-action estimating unit 80 and a procedure supporting unit 90.

The procedure-action estimating unit 80 estimates actions in a procedure performed by an operator based on information from the medical device. The procedure-action estimating unit 80 includes a treatment-tool identifying unit 81 that identifies a kind of treatment tool that appears in an endoscopic image corresponding to an image signal included in information from the medical device, and an estimating unit 82 that estimates an action of the operator based on a determination result of the treatment-tool identifying unit 81.

The procedure supporting unit 90 supports a procedure by the operator according to an estimation result of the procedure-action estimating unit 80. The procedure supporting unit 90 includes a forceps-procedure supporting unit 91, a snare-procedure supporting unit 92, a local-injection procedure supporting unit 93, an energy-device-procedure supporting unit 94, and a hemostasis-procedure supporting unit 95.

The forceps-procedure supporting unit 91 performs, when the estimating unit 82 estimates as a forceps-procedure, a support according to a procedure with forceps. The forceps-procedure supporting unit 91 includes a surface-blood-vessel highlighting unit 911 that highlights surface blood vessels.

The snare-procedure supporting unit 92 performs, when the estimating unit 82 estimates as a snare procedure, a support according to a procedure with a snare. The snare-procedure supporting unit 92 includes a surface-blood-vessel highlighting unit 921 that highlights surface blood vessels.

The local-injection procedure supporting unit 93 performs, when the estimating unit 82 estimates as a local injection procedure, a support according to a local injection procedure. The local-injection procedure supporting unit 93 includes a surface-blood-vessel highlighting unit 931 that highlights surface blood vessels. A treatment tool used in the local injection procedure is an injection needle.

The energy-device-procedure supporting unit 94 performs, when the estimating unit 82 estimates as a procedure with an energy device, a support according to a procedure with the energy device. The energy-device-procedure supporting unit 94 includes a deep-blood-vessel highlighting unit 941 that highlights deep blood vessels. A treatment tool used in the procedure with an energy device is either a high frequency knife or an ultrasonic device. In the following, a case in which a high frequency knife is used as the energy device will be described.

The hemostasis-procedure supporting unit 95 performs, when the estimating unit 82 estimates as a hemostasis procedure, a support according to a procedure with a hemostasis device. The hemostasis-procedure supporting unit 95 includes a bleeding-origin highlighting unit 951 that highlights a bleeding origin. A treatment tool used in the hemostasis procedure is a clip and an APC probe.

Processing by Image Processing Apparatus

Figure 3:
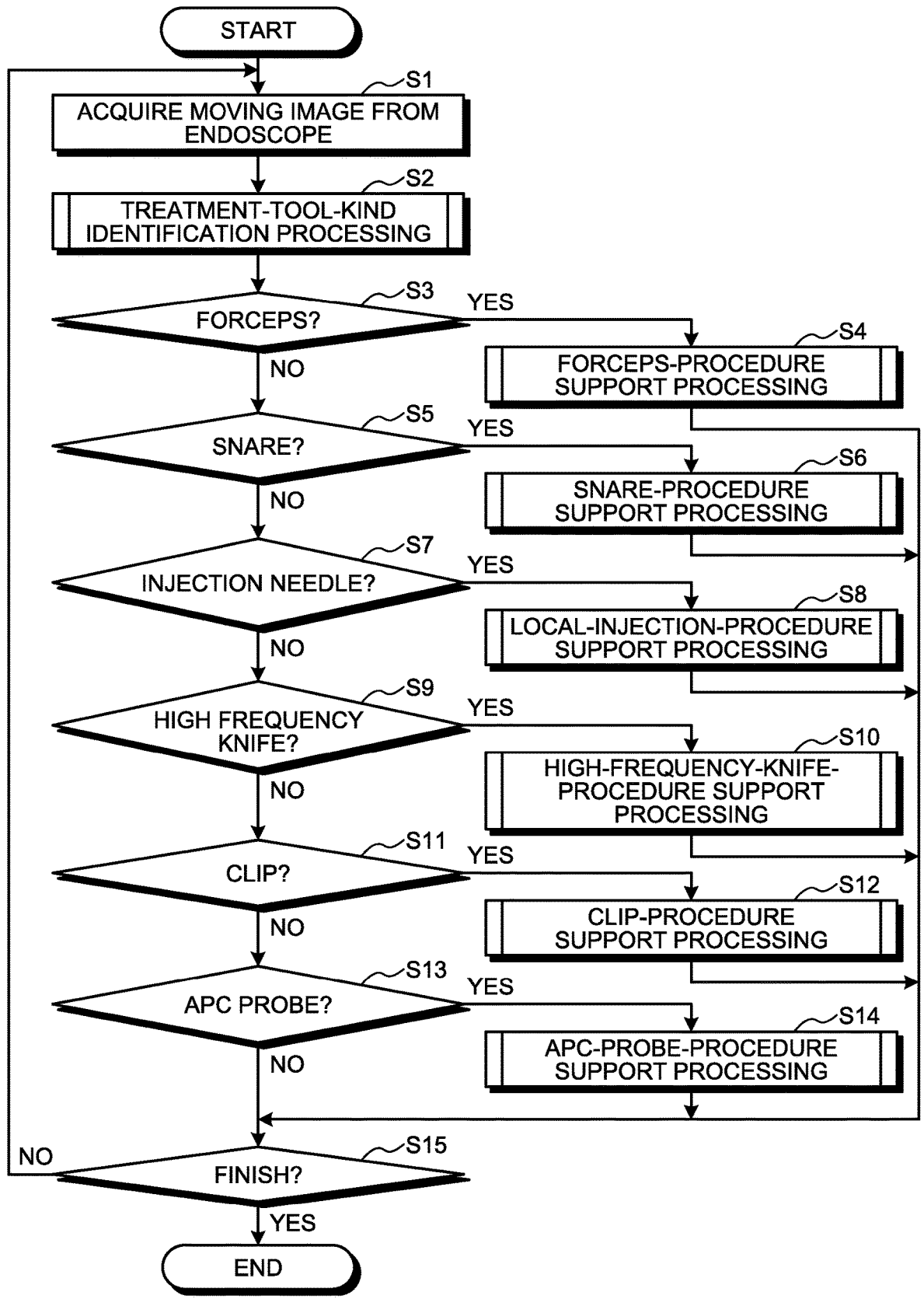
FIG. 3 is a flowchart illustrating an overview of processing performed by the image processing apparatus according to the first embodiment of the disclosure.

Next, processing performed by the image processing apparatus 1 will be described. FIG. 3 is a flowchart illustrating an overview of the processing performed by the image processing apparatus 1.

As illustrated in FIG. 3, first, the acquiring unit 20 acquires a moving image from the medical device (step S1). The moving image herein is a group of chronologically successive endoscopic images.

Subsequently, the procedure-action estimating unit 80 performs treatment-tool identification processing to identify the kind of treatment tool that appears in an endoscopic image based on the moving image acquired by the acquiring unit 20 (step S2). After step S2, the image processing apparatus 1 shifts to step S3.

Treatment-Tool Identification Processing

Figure 4:
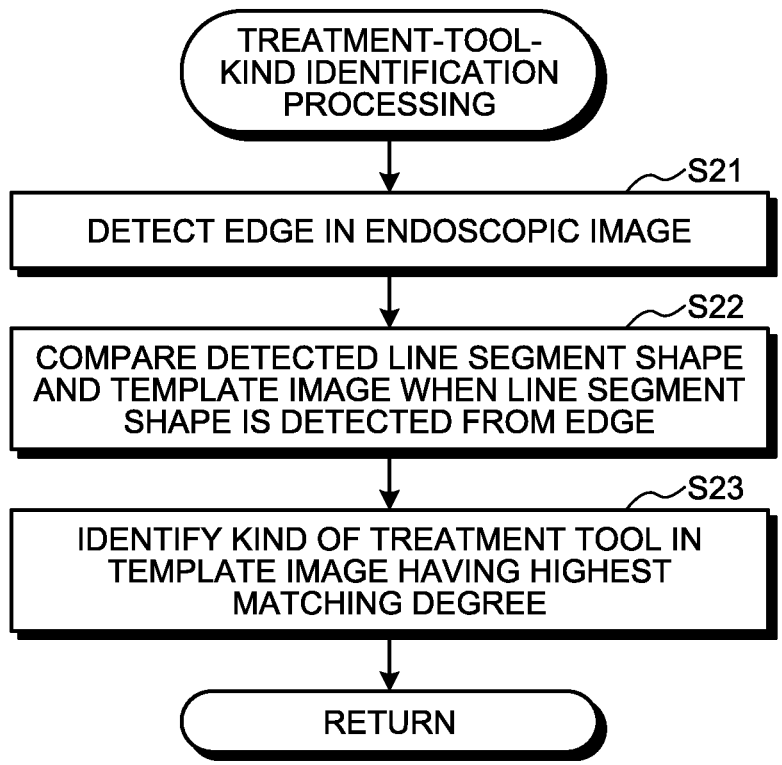
FIG. 4 is a flowchart illustrating an overview of treatment-tool-kind identification processing in FIG. 3.

FIG. 4 is a flowchart illustrating an overview of the treatment-tool identification processing at step S2 in FIG. 3 described above.

As illustrated in FIG. 4, the treatment-tool identifying unit 81 detects edges in an endoscopic image (step S21). Specifically, first, the treatment-tool identifying unit 81 detects edges in an endoscopic image by a publicly-known edge extraction method (reference: *DIGITAL IMAGE PROCESSING* [revised new version], CG-ARTS society: p. 105, Edge Extraction) or the like.

Subsequently, the treatment-tool identifying unit 81 compares, when a line segment shape is detected from the edges detected at step S21, the detected line segment shape and a template image by image recognition (step S22). Specifically, first, the treatment-tool identifying unit 81 calculates linearity by a publicly-known Hough transform (reference: *DIGITAL IMAGE PROCESSING* [revised new version], CG-ARTS society: p. 238, Hough Transform) from the edges detected at step S21. The treatment-tool identifying unit 81 then detects one having linearity equal to or higher than a predetermined value, as the line segment shape, and compares this detected line segment shape with template images of line segment shapes of respective treatment tools prepared in advance. The treatment tools are forceps, a snare, an injection needle, a high frequency knife as an energy device, a clip and an APC probe as a hemostatic device. Moreover, a comparing method by the treatment-tool identifying unit 81 is a publicly-known template matching (reference: *DIGITAL IMAGE PROCESSING* [revised new version], CG-ARTS society: p. 218, Pattern Detection by Template Matching), or the like.

Thereafter, the treatment-tool identifying unit 81 identifies a kind of treatment tool of a template image having the highest matching degree in the template matching performed at step S22 (step S23). As for the matching degree, for example, when template images are binary images, a total sum of exclusive disjunction is calculated, and it is determined that the matching degree is high when a calculation result from this calculation is small. Moreover, even when template images are 8-bit images or color images, by using a publicly-known similarity, such as SSD (*DIGITAL IMAGE PROCESSING* [revised new version], CG-ARTS society: p. 219, Similarity), the treatment-tool identifying unit 81 may determine that the matching degree is high when a resultant is small. After step S23, the image processing apparatus 1 returns to step S2 in FIG. 3.

Referring back to FIG. 3, procedures at step S3 and later will be described.

At step S3, when the estimating unit 82 estimates that the operator is using forceps based on the identification result of the treatment-tool identifying unit 81 (step S3: YES), the forceps-procedure supporting unit 91 performs forceps-procedure support processing in which a support according to a procedure with forceps is performed (step S4). After step S4, the image processing apparatus 1 shifts to step S15 described later. On the other hand, when the estimating unit 82 estimates that the operator is not using forceps based on the identification result of the treatment-tool identifying unit 81 (step S3: NO), the image processing apparatus 1 shifts to step S5 described later.

Forceps-Procedure Support Processing

Figure 5:
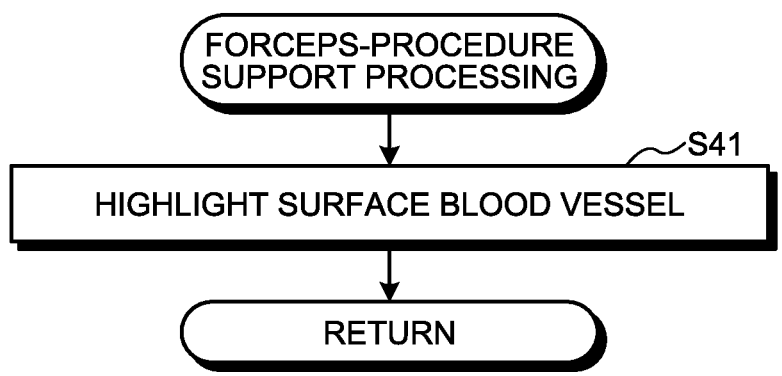
FIG. 5 is a flowchart illustrating an overview of forceps-procedure support processing in FIG. 3.

FIG. 5 is a flowchart illustrating an overview of the forceps-procedure support processing at step S4 in FIG. 3 described above. As illustrated in FIG. 5, the surface-blood-vessel highlighting unit 911 switches to processing of highlighting a surface blood vessel (step S41). Specifically, the surface-blood-vessel highlighting unit 911 outputs an instruction signal to cause the light source device 4 to irradiate special light (narrow band light) including a narrow band light having the center wavelength of 415 nm and a narrow band light having the center wavelength of 540 nm, through the output unit 40. Furthermore, the surface-blood-vessel highlighting unit 911 generates an image by performing image processing of highlighting surface blood vessels based on an endoscopic image generated by the endoscope 2 when the special light is irradiated, and then outputs the generated image to the display device 3 through the output unit 40. Thus, in the endoscope system 100, the endoscope 2 captures a subject of imaging (living tissue) under irradiation with the special light, and an image in which a surface blood vessel appearing in this captured endoscopic image is highlighted is displayed on the display device 3. The surface-blood-vessel highlighting unit 911 may be configured to generate a highlighted image in which a surface blood vessel is highlighted by using a publicly-known image processing technique with respect to an endoscopic image, and to output this generated highlighted image to the display device 3. After step S41, the image processing apparatus 1 returns to step S4 in FIG. 3.

Referring back to FIG. 3, procedures at step S5 and later will be described.

At step S5, when the estimating unit 82 estimates that the operator is using a snare based on the identification result of the treatment-tool identifying unit 81 (step S5: YES), the snare-procedure supporting unit 92 performs snare-procedure support processing in which a support according to a procedure with a snare is performed (step S6). After step S6, the image processing apparatus 1 shifts to step S15 described later. On the other hand, when the estimating unit 82 estimates that the operator is not using a snare based on the identification result of the treatment-tool identifying unit 81 (step S5: NO), the image processing apparatus 1 shifts to step S7 described later.

Snare-Procedure Support Processing

FIG. 6 is a flowchart illustrating an overview of the snare-procedure support processing at step S6 in FIG. 3 described above. As illustrated in FIG. 6, the surface-blood-vessel highlighting unit 921 switches to processing of highlighting a surface blood vessel (step S61). Specifically, the surface-blood-vessel highlighting unit 921 performs processing similar to that at step S41 in FIG. 5 described above. After step S61, the image processing apparatus 1 returns to the main routine in FIG. 3.

Referring back to FIG. 3, procedures at step S7 and later will be describe.

At step S7, when the estimating unit 82 estimates that the operator is using an injection needle based on the identification result of the treatment-tool identifying unit 81 (step S7: YES), the local-injection-treatment supporting unit 93 performs local-injection-procedure support processing according to a procedure with an injection needle (step S8). After step S8, the image processing apparatus 1 shifts to step S15 described later. On the other hand, when the estimating unit 82 estimates that the operator is not using an injection needle based on the identification result of the treatment-tool identifying unit 81 (step S7: NO), the image processing apparatus 1 shifts to step S9 described later.

Local-Injection-Procedure Support Processing

FIG. 7 is a flowchart illustrating an overview of the local-injection-procedure support processing at step S8 in FIG. 3 described above. As illustrated in FIG. 7, the surface-blood-vessel highlighting unit 931 switches to processing of highlighting a surface blood vessel (step S81). Specifically, the surface-blood-vessel highlighting unit 931 performs processing similar to that at step S41 in FIG. 5 described above. After step S81, the image processing apparatus 1 returns to the main routine in FIG. 3.

Referring back to FIG. 3, procedures at step S9 and later will be describe.

At step S9, when the estimating unit 82 estimates that the operator is using a high frequency knife based on the identification result of the treatment-tool identifying unit 81 (step S9: YES), the energy-device-procedure supporting unit 94 performs high-frequency-knife-procedure support processing to support a procedure with a high frequency knife (step S10). After step S10, the image processing apparatus 1 shifts to step S15 described later. On the other hand, when the estimating unit 82 estimates that the operator is not using a high frequency knife based on the identification result of the treatment-tool identifying unit 81 (step S9: NO), the image processing apparatus 1 shifts to step S11 described later.

High-Frequency-Knife-Procedure Support Processing

Figure 8:
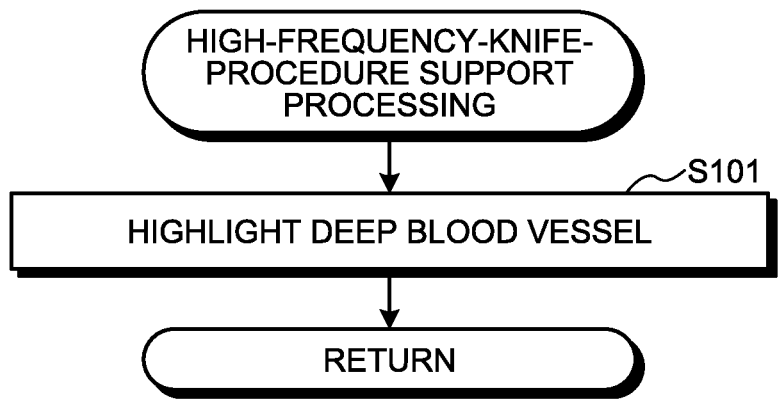
FIG. 8 is a flowchart illustrating an overview of high-frequency-knife-procedure support processing in FIG. 3.

FIG. 8 is a flowchart illustrating an overview of the high-frequency-knife-procedure support processing at step S10 in FIG. 3 described above. As illustrated in FIG. 8, the deep-blood-vessel highlighting unit 941 switches to processing of highlighting a deep blood vessel (step S101). Specifically, the deep-blood-vessel highlighting unit 941 outputs an instruction signal to cause the light source device 4 to irradiate special light including a narrow band light of a wavelength band around 85 nm to 615 nm and a narrow band light of a wavelength band around 610 nm to 730 nm (for example, refer to JP-T-2013-522028), through the output unit 40. Furthermore, the deep-blood-vessel highlighting unit 941 generates a deep-blood-vessel highlighted image by performing image processing of highlighting deep blood vessels based on an endoscopic image generated by the endoscope 2 when the special light is irradiated, and then outputs the generated deep-blood-vessel highlighted image to the display device 3 through the output unit 40. Thus, an image in which a deep blood vessel is highlighted can be displayed on the display device 3. The deep-blood-vessel highlighting unit 941 may be configured to generate a highlighted image in which a deep blood vessel is highlighted by using a publicly-known image processing technique with respect to an endoscopic image, and to output this generated highlighted image to the display device 3. After step S101, the image processing apparatus 1 returns to the main routine in FIG. 3.

Referring back to FIG. 3, procedures at step S11 and later will be describe.

At step S11, when the estimating unit 82 estimates that the operator is using a clip based on the identification result of the treatment-tool identifying unit 81 (step S11: YES), the hemostasis-procedure supporting unit 95 performs clip-procedure support processing to support a procedure with a clip (step S12). After step S12, the image processing apparatus 1 shifts to step S15 described later. On the other hand, when the estimating unit 82 estimates that the operator is not using a clip based on the identification result of the treatment-tool identifying unit 81 (step S11: NO), the image processing apparatus 1 shifts to step S13 described later.

Clip-Procedure Support Processing

Figure 9:
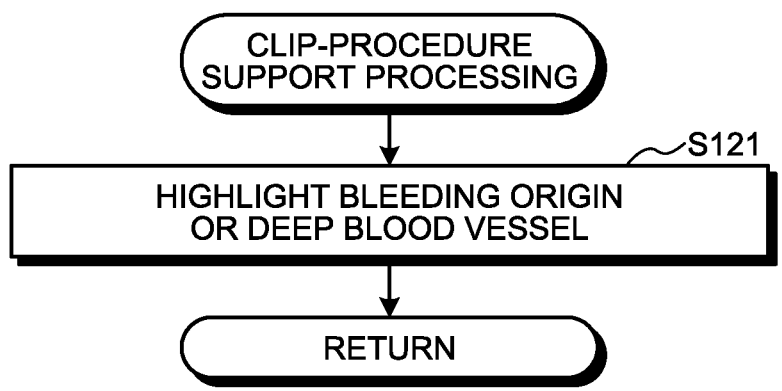
FIG. 9 is a flowchart illustrating an overview of clip-procedure support processing in FIG. 3.

FIG. 9 is a flowchart illustrating an overview of the clip-procedure support processing at step S12 in FIG. 3. As illustrated in FIG. 9, the bleeding-origin highlighting unit 951 switches to processing of highlighting a bleeding origin or a deep blood vessel (step S121). Specifically, the bleeding-origin highlighting unit 951 performs processing similar to that at step S101 in FIG. 8 described above. After step S121, the image processing apparatus 1 returns to the main routine in FIG. 3.

Referring back to FIG. 3, procedures at step S13 and later will be describe.

At step S13, when the estimating unit 82 estimates that the operator is using an APC probe based on the identification result of the treatment-tool identifying unit 81 (step S13: YES), the hemostasis-procedure supporting unit 95 performs APC-probe-procedure support processing to support a procedure with an APC probe (step S14). After step S14, the image processing apparatus 1 shifts to step S15 described later. On the other hand, when the estimating unit 82 estimates that the operator is not using an APC probe based on the identification result of the treatment-tool identifying unit 81 (step S13: NO), the hemostasis-procedure supporting unit 95 shifts to step S15 described later.

APC-Probe-Procedure Support Processing

Figure 10:
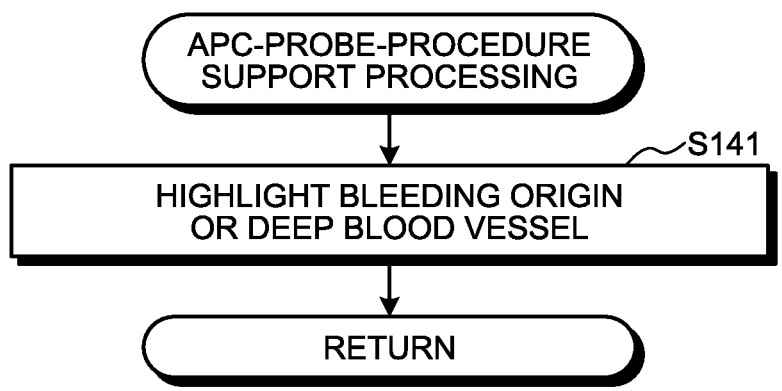
FIG. 10 is a flowchart illustrating an overview of APC-probe-procedure processing in FIG. 3.

FIG. 10 is a flowchart illustrating an overview of the APC-probe-procedure processing at step S14 in FIG. 3. As illustrated in FIG. 10, the bleeding-origin highlighting unit 951 switches to processing of highlighting a bleeding origin or a deep blood vessel (step S141). Specifically, the bleeding-origin highlighting unit 951 performs processing similar to that at step S101 in FIG. 8 described above. After step S141, the image processing apparatus 1 returns to the main routine in FIG. 3.

Referring back to FIG. 3, procedures at step S15 and later will be describe.

At step S15, when the treatment of the subject is to be finished in accordance with an operation of the input unit 30 (step S15: YES), the image processing apparatus 1 ends the processing. On the other hand, when the treatment of the subject is not to be finished in accordance with an operation of the input unit 30 (step S15: NO), the image processing apparatus 1 returns to step S1 described above.

According to the first embodiment of the disclosure described above, a support according to various procedures in endoscopy performed by an operator can be provided.

Second Embodiment

Next, a second embodiment of the disclosure will be described. An image processing apparatus according to the second embodiment differs in a configuration from the arithmetic unit 70 of the image processing apparatus 1 according to the first embodiment described above. Hereinafter, a configuration of the image processing apparatus according to the second embodiment will be described, and then processing performed by the image processing apparatus according to the second embodiment will be described. Note that the same reference symbols are assigned to the same components as the image processing apparatus 1 according to the first embodiment described above, and description thereof is omitted.

Configuration of Image Processing Apparatus]

Figure 11:
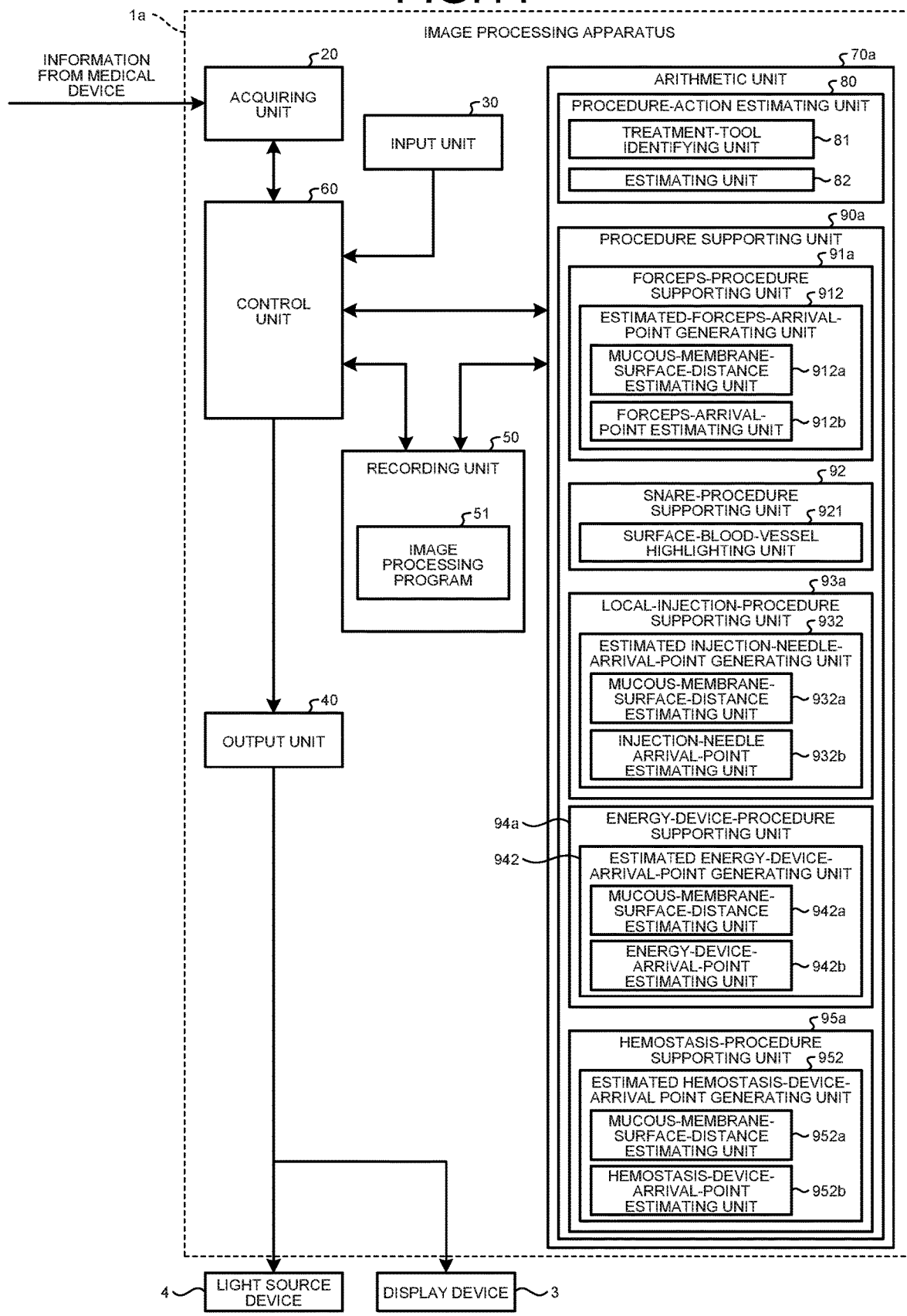
FIG. 11 is a block diagram illustrating a configuration of an image processing apparatus according to a second embodiment of the disclosure.

FIG. 11 is a block diagram illustrating a configuration of the image processing apparatus according to the second embodiment of the disclosure. An image processing apparatus 1a illustrated in FIG. 11 includes an arithmetic unit 70a in place of the arithmetic unit 70 in the image processing apparatus 1 according to the first embodiment described above.

Detailed Configuration of Arithmetic Unit

The arithmetic unit 70a includes a procedure supporting unit 90a in place of the procedure supporting unit 90 according to the first embodiment described above. The procedure supporting unit 90a supports a procedure by an operator according to an estimation result by the procedure-action estimating unit 80. The procedure supporting unit 90a includes a forceps-procedure supporting unit 91a, a local-injection procedure supporting unit 93a, an energy-device-procedure supporting unit 94a, and a hemostasis-procedure supporting unit 95a in place of the forceps-procedure supporting unit 91, the local-injection procedure supporting unit 93, the energy-device-procedure supporting unit 94, and the hemostasis-procedure supporting unit 95 according to the first embodiment described above.

The forceps-procedure supporting unit 91a performs, when the estimating unit 82 estimates as a forceps procedure, a support according to a procedure with forceps. The forceps-procedure supporting unit 91a includes an estimated-forceps-arrival-point generating unit 912 that outputs an estimated point at which the forceps reach a mucous membrane surface to the display device 3. Furthermore, the estimated-forceps-arrival-point generating unit 912 includes a mucous-membrane-surface-distance estimating unit 912a that estimates an imaging distance at respective pixel coordinates in an endoscopic image, and a forceps-arrival-point estimating unit 912b that estimates an arrival point of forceps based on a positional relation between an optical center of the endoscope 2 and the forceps inlet (the treatment channel at the distal end portion 202 of the endoscope 2), and the imaging distance to a mucous membrane surface.

The local-injection procedure supporting unit 93a performs, when the estimating unit 82 estimates as a local injection procedure, a support according to a local injection procedure. The local-injection procedure supporting unit 93a includes an estimated injection-needle-arrival-point generating unit 932 that outputs an estimated point at which an injection needle reaches a mucous membrane surface, to the display device 3. Furthermore, the estimated injection-needle-arrival-point generating unit 932 includes a mucous-membrane-surface-distance estimating unit 932a that estimates an imaging distance at respective pixel coordinates in an endoscopic image, and an injection-needle arrival-point estimating unit 932b that estimates an arrival point of an injection needle based on a positional relation between the optical center of the endoscope 2 and the forceps inlet, and the imaging distance to a mucous membrane surface.

The energy-device-procedure supporting unit 94a performs, when the estimating unit 82 estimates as an energy device procedure, a support according to a procedure with an energy device. The energy-device-procedure supporting unit 94a includes an estimated energy-device-arrival-point generating unit 942 that outputs an estimated point at which an energy device reaches a mucous membrane surface, to the display device 3. Furthermore, the estimated energy-device-arrival-point generating unit 942 includes a mucous-membrane-surface-distance estimating unit 942*a* that estimates an imaging distance at respective pixel coordinates in an endoscopic image, and an energy-device-arrival-point estimating unit 942*b* that estimates an arrival point of an energy device based on a positional relation between the optical center of the endoscope 2 and the forceps inlet, and the imaging distance to a mucous membrane surface.

The hemostasis-procedure supporting unit 95*a* performs, when the estimating unit 82 estimates as a hemostasis procedure, a support according to a procedure with a hemostasis device. The hemostasis-procedure supporting unit 95*a* includes an estimated hemostasis-device-arrival point generating unit 952 that outputs an estimated point at which a hemostasis device reaches a mucous membrane surface, to the display device 3. Furthermore, the estimated hemostasis-device-arrival point generating unit 952 includes a mucous-membrane-surface-distance estimating unit 952*a* that estimates an imaging distance at respective pixel coordinates in an endoscopic image, and a hemostasis-device-arrival-point estimating unit 952*b* that estimates an arrival point of a hemostasis device based on a positional relation between the optical center of the endoscope 2 and the forceps inlet, and the imaging distance to a mucous membrane surface.

Processing of Image Processing Apparatus

Next, processing performed by the image processing apparatus 1*a* will be described. The image processing apparatus 1*a* performs processing similar to that of the image processing apparatus 1 according to the first embodiment described above, but differs in each of the forceps-procedure support processing in FIG. 5, the local-injection-procedure support processing in FIG. 7, the high-frequency-knife-procedure support processing in FIG. 8, the clip-procedure support processing in FIG. 9, and the APC-probe-procedure support processing in FIG. 10 described above. Hereinafter, the forceps-procedure support processing, the local-injection-procedure support processing, the high-frequency-knife-procedure support processing, the clip-procedure support processing, and the APC-probe-procedure support processing performed by the image processing apparatus 1*a* will be described.

Forceps-Procedure Support Processing

Figure 12:
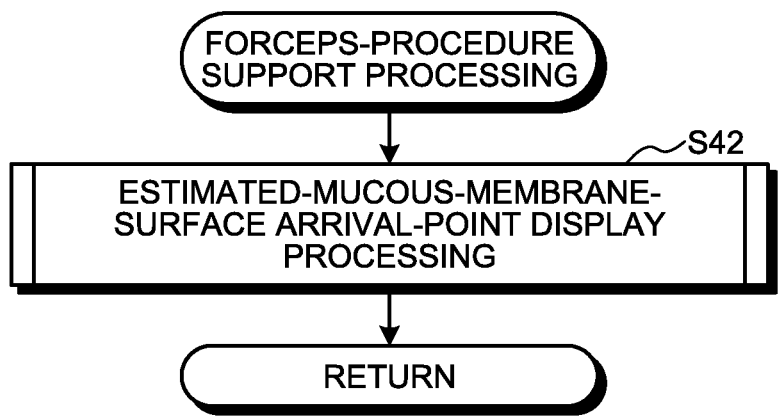
FIG. 12 is a flowchart illustrating an overview of forceps-procedure support processing performed by an estimated-forceps-arrival-point generating unit according to the second embodiment of the disclosure.

First, the forceps-procedure support processing performed by the image processing apparatus 1*a* will be described. FIG. 12 is a flowchart illustrating an overview of the forceps-procedure support processing performed by the estimated-forceps-arrival-point generating unit 912.

As illustrated in FIG. 12, the estimated-forceps-arrival-point generating unit 912 performs estimated-mucous-membrane-surface arrival-point display processing of outputting an estimated point at which forceps reach a mucous membrane surface to the display device 3 (step S42). After step S42, the image processing apparatus 1*a* returns to the main routine in FIG. 3.

Estimated-Mucous-Membrane-Surface Arrival-Point Display Processing

Figure 13:
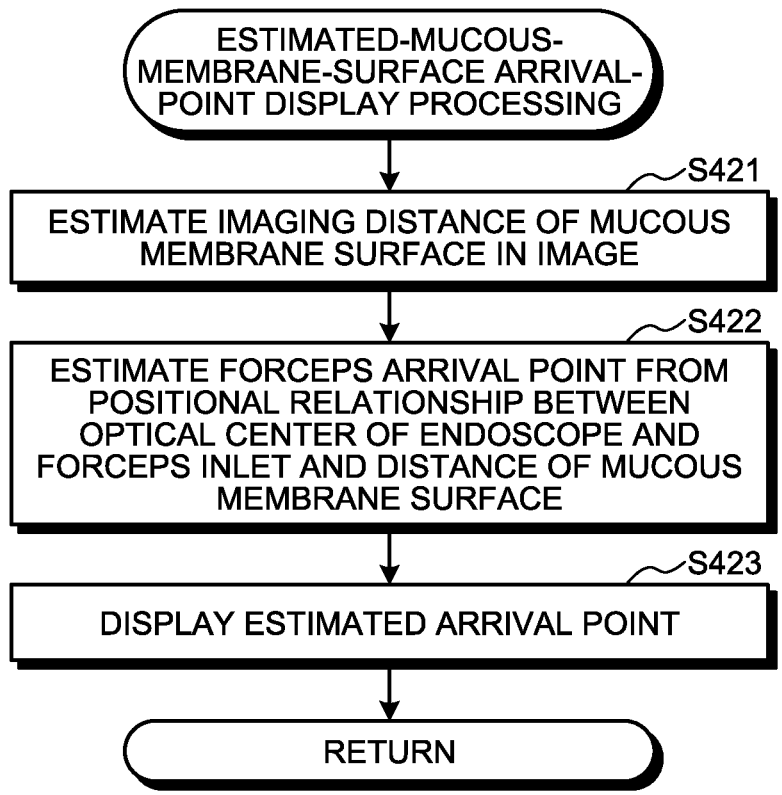
FIG. 13 is a flowchart illustrating an overview of an estimated-mucous-membrane-surface arrival-point display processing in FIG. 12.

FIG. 13 is a flowchart illustrating an overview of the estimated-mucous-membrane-surface arrival-point display processing at step S42 in FIG. 12. As illustrated in FIG. 13, the mucous-membrane-surface-distance estimating unit 912*a* estimates an imaging distance at respective pixel coordinates in an endoscopic image (step S421). Specifically, the mucous-membrane-surface-distance estimating unit 912*a* selects a low-absorption wavelength (for example, R) component, the degree of absorption and scattering of which in a living body is the lowest, as a low-absorption wavelength component. The reasons for this is to acquired pixel value information having the highest correlation with an imaging distance from the mucous membrane surface by suppressing decrease of a pixel value by a blood vessel appearing on the mucous membrane surface of a living body, and the like, and because an R component is a component having a wavelength apart from an absorption band of a blood vessel, and of a long wavelength in an image composed of R, G, B components, and is less prone to be affected by absorption and scattering in a living body. The mucous-membrane-surface-distance estimating unit 912*a* then estimates an imaging distance, assuming a Lambertian surface based on a pixel value of a low-absorption wavelength component. Specifically, the mucous-membrane-surface-distance estimating unit 912*a* estimates an imaging distance at respective pixel coordinates in an endoscopic image by calculation based on Equation (1) below.

$$\alpha = \sqrt{\frac{I \times K \times \cos\theta}{L}} \qquad (1)$$

Herein, α expresses an imaging distance, I expresses a radiation intensity (it is measured and recorded in the recording unit 50 in advance) of a light source (the light source device 4), K expresses a defuse reflection coefficient (it is measured and recorded in the recording unit 50 in advance) on a mucous membrane surface, θ expresses an angle formed between a normal vector on a mucous membrane surface and a vector from the mucous membrane surface to the light source (illumination lens) (an average value is set in advance although it is a value determined by a positional relationship of the light source of the endoscope 2 and a mucous membrane surface), and L expresses an R component value of a pixel in which the mucous membrane surface of a subject to distance estimation appears. Note that the mucous-membrane-surface-distance estimating unit 912*a* estimates an imaging distance based on an endoscopic image, assuming a subject to imaging as a Lambertian surface, but it is not limited thereto. An imaging distance to a mucous membrane surface in an endoscopic image may be estimated by using various publicly-known techniques. Moreover, the mucous-membrane-surface-distance estimating unit 912*a* may perform correction of pixel value non-uniformity caused by an optical system and an illumination system that can cause reduction of accuracy in the respective processing, and removal of non-mucous-membrane region, such as mirror reflection, dregs, and bubbles, before estimation of an imaging distance to a mucous membrane surface. Furthermore, besides estimating an imaging distance to a mucous membrane surface by image processing, the mucous-membrane-surface-distance estimating unit 912*a* may calculate it by using a distance measuring sensor, or the like. Moreover, not necessarily performing estimation of the imaging distance to a mucous membrane surface, the mucous-membrane-surface-distance estimating unit 912*a* may perform adaptive processing at a later stage with a pixel value having a correlation with a distance.

Figure 14:
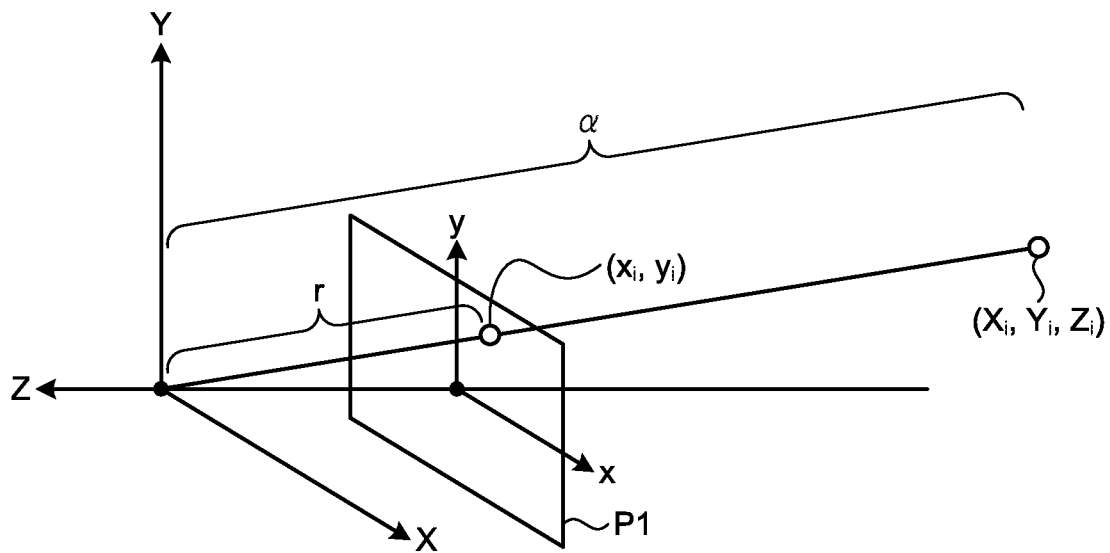
FIG. 14 is a diagram schematically illustrating a relationship for estimating surface coordinates of a mucous membrane surface appearing in respective pixels in an endoscopic image.

Subsequently, the forceps-arrival-point estimating unit 912*b* estimates an arrival point of forceps based on a positional relationship between the optical center of the endoscope 2 and the forceps inlet (the treatment tool channel) and the imaging distance at respective pixel coordinates in the endoscopic image estimated at step S421 (step S422). Between coordinates ($x_i$, $y_i$) in an endoscopic image (the origin 0 is a center of an endoscopic image P1) and surface coordinates $(X_i, Y_i, Z_i)$ of a subject appearing at the coordinates, there is a relationship illustrated in FIG. 14. XYZ are a surface coordinate system constituted of an XY axis parallel to an xy axis of the endoscopic image P1, and a Z axis passing through the center of the endoscopic image P1. Moreover, r is a value determined from a pixel pitch of an imaging device (not shown) of the endoscope 2, characteristics of an imaging system (not shown) of the endoscope 2, and the like. $\alpha$ is an imaging distance estimated at step S421 described above. Therefore, from the relationship in FIG. 14, Equation (2) and Equation (3) below hold.

$$\frac{a}{r} = \frac{X_i}{x_i} = \frac{Y_i}{y_i} = \frac{Z_i}{f} \quad (2)$$

$$r = \sqrt{x_j^2 + y_i^2 + f^2} \quad (3)$$

Because a positional relationship $(T_x, T_y)$ between the Z axis and a forceps inlet 22 has been measured previously, or has been known, if a value $T_z$ in the z axis direction is acquired, a forceps arrival point in space can be determined as "T $(T_x, T_y, T_z)$, and a forceps arrival point on the endoscopic image P1 can be determined as $t(t_x, t_y)$.

Moreover, the forceps-arrival-point estimating unit 912b calculates a position $(X_i, Y_i, Z_i)$ in space of respective pixels based on the imaging distance to the mucous membrane surface in the endoscopic image from the imaging unit of the endoscope estimated by the mucous-membrane-surface-distance estimating unit 912a at step S421 described above, and on Equation (4) below based on Equation (2) and Equation (3) described above.

$$\begin{pmatrix} X_j \\ Y_i \\ Z_i \end{pmatrix} = \frac{\alpha}{\sqrt{x_j^2 + y_i^2 + f^2}} \begin{pmatrix} x_i \\ y_i \\ f \end{pmatrix} \quad (4)$$

As described, the forceps-arrival-point estimating unit 912b can determine an X coordinate, a Y coordinate, and a Z coordinate in space with respect to entire coordinates in the endoscopic image P1. Based on that, the forceps-arrival-point estimating unit 912b estimates coordinates in an image having an X coordinate and a Y coordinate that match with, or that are present within a predetermined distance (the shortest distance) to an X coordinate Tx and a Y coordinate Ty in space, as the forceps arrival point $t(t_x, t_y)$ of the endoscopic image P1.

Thereafter, the forceps-procedure supporting unit 91a outputs the estimated arrival point of the forceps estimated at step S422 to the display device 3 through the output unit 40, thereby causing the display device 3 to display it (step S423). After step S423, the image processing apparatus 1a returns to a subroutine in FIG. 12.

Local-Injection-Procedure Support Processing

Figure 15:
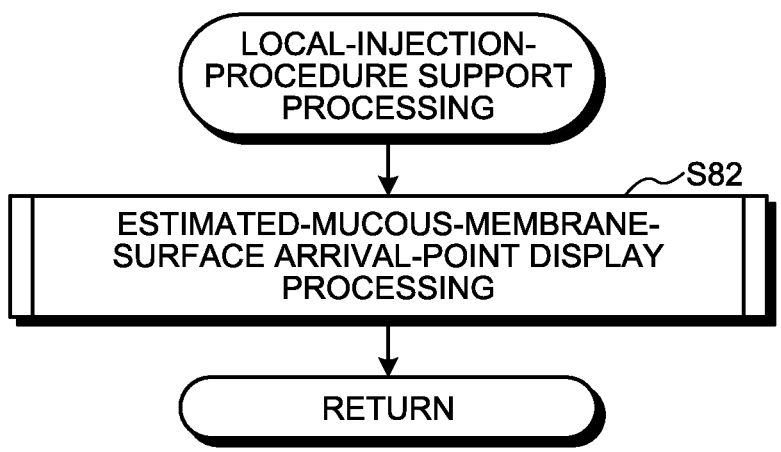
FIG. 15 is a flowchart illustrating an overview of local-injection-procedure support processing performed by an estimated injection-needle-arrival-point generating unit according to the second embodiment of the disclosure.

Next, the local-injection-procedure support processing performed by the image processing apparatus 1a will be described. FIG. 15 is a flowchart illustrating an overview of the local-injection-procedure support processing performed by an estimated injection-needle-arrival-point generating unit 932.

As illustrated in FIG. 15, the estimated injection-needle-arrival-point generating unit 932 performs the estimated-mucous-membrane-surface arrival-point display processing to output an estimated point at which an injection needle reaches a mucous membrane surface, to the display device 3 (step S82). Specifically, the mucous-membrane-surface-distance estimating unit 932a and the injection-needle arrival-point estimating unit 932b perform processing similar to the estimated-mucous-membrane-surface arrival-point display processing in FIG. 13 described above. After step S82, the image processing apparatus 1a returns to the main routine in FIG. 3.

High-Frequency-Knife-Procedure Support Processing

Figure 16:
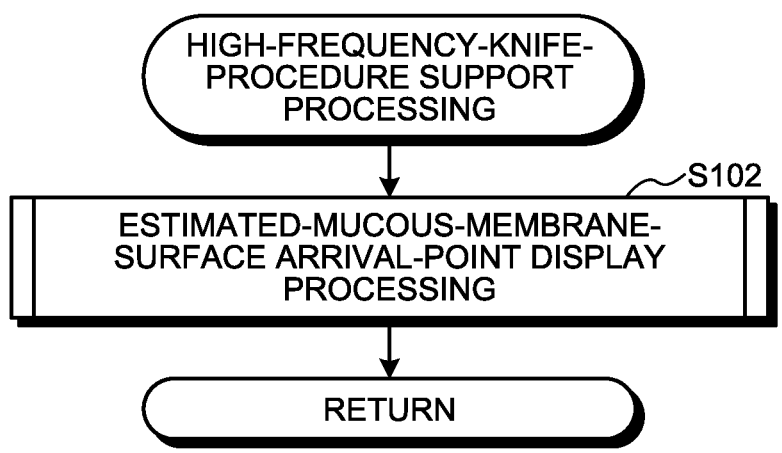
FIG. 16 is a flowchart illustrating an overview of high-frequency-knife-procedure support processing performed by an estimated energy-device-arrival-point generating unit according to the second embodiment of the disclosure.

Next, the high-frequency-knife-procedure support processing performed by the estimated energy-device-arrival-point generating unit 942 will be described. FIG. 16 is a flowchart illustrating an overview of the high-frequency-knife-procedure support processing performed by the estimated energy-device-arrival-point generating unit 942.

As illustrated in FIG. 16, the estimated energy-device-arrival-point generating unit 942 performs the estimated-mucous-membrane-surface arrival-point display processing to output an estimated point at which a high frequency knife reaches a mucous membrane surface, to the display device 3 (step S102). Specifically, the mucous-membrane-surface-distance estimating unit 942a and the energy-device-arrival-point estimating unit 942b perform processing similar to the estimated-mucous-membrane-surface arrival-point display processing in FIG. 13 described above. After step S102, the image processing apparatus 1a returns to the main routine in FIG. 3.

Clip-Procedure Support Processing

Figure 17:
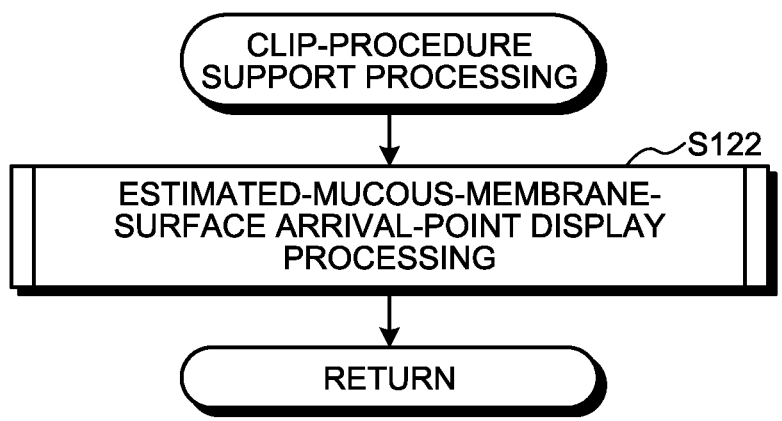
FIG. 17 is a flowchart illustrating an overview of clip-procedure support processing performed by an estimated hemostasis-device-arrival point generating unit according to the second embodiment of the disclosure.

Next, the clip-procedure support processing performed by the estimated hemostasis-device-arrival point generating unit 952 will be described. FIG. 17 is a flowchart illustrating an overview of the clip-procedure support processing performed by the estimated hemostasis-device-arrival point generating unit 952.

As illustrated in FIG. 17, the estimated hemostasis-device-arrival point generating unit 952 performs the estimated-mucous-membrane-surface arrival-point display processing to output an estimated point at which a clip reaches a mucous membrane surface, to the display device 3 (step S122). Specifically, the mucous-membrane-surface-distance estimating unit 952a and the hemostasis-device-arrival-point estimating unit 952b perform processing similar to the estimated-mucous-membrane-surface arrival-point display processing in FIG. 13 described above. After step S122, the image processing apparatus 1a returns to the main routine in FIG. 3.

APC-Probe-Procedure Support Processing

Figure 18:
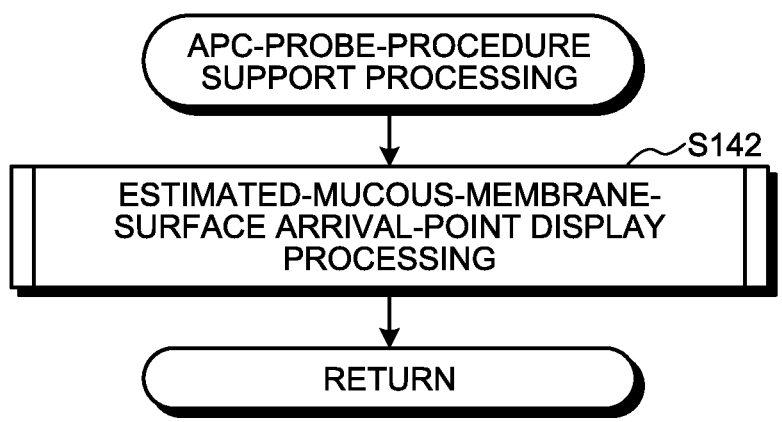
FIG. 18 is a flowchart illustrating an overview of APC-probe-procedure support processing performed by the estimated hemostasis-device-arrival point generating unit according to the second embodiment of the disclosure.

Next, the APC-probe-procedure support processing performed by the estimated hemostasis-device-arrival point generating unit 952 will be described. FIG. 18 is a flowchart illustrating an overview of the APC-probe-procedure support processing performed by the estimated hemostasis-device-arrival point generating unit 952.

As illustrated in FIG. 18, the estimated hemostasis-device-arrival point generating unit 952 performs the estimated-mucous-membrane-surface arrival-point display processing to output an estimated point at which an APC probe reaches a mucous membrane surface, to the display device 3 (step S142). Specifically, the mucous-membrane-surface-distance estimating unit 952a and the hemostasis-device-arrival-point estimating unit 952b perform processing similar to the estimated-mucous-membrane-surface arrival-point display processing in FIG. 13 described above. After step S142, the image processing apparatus 1a returns to the main routine in FIG. 3.

According to the second embodiment of the disclosure described above, a support according to various procedures in endoscopy performed by an operator can be provided.

Moreover, according to the second embodiment of the disclosure, an estimated point at which a treatment tool reaches a mucous membrane surface is displayed and, therefore, a support for an operator to perform a procedure speedily can be provided.

Third Embodiment

Next, a third embodiment of the disclosure will be described. An image processing apparatus according to the third embodiment differs in a configuration from the arithmetic unit 70 in the image processing apparatus 1 according to the first embodiment described above. Hereinafter, a configuration of the image processing apparatus according to the third embodiment will be described, and then processing performed by the image processing apparatus according to the third embodiment will be described. Note that the same reference symbols are assigned to the same components as the image processing apparatus 1 according to the first embodiment described above, and description thereof is omitted.

Configuration of Image Processing Apparatus

Figure 19:
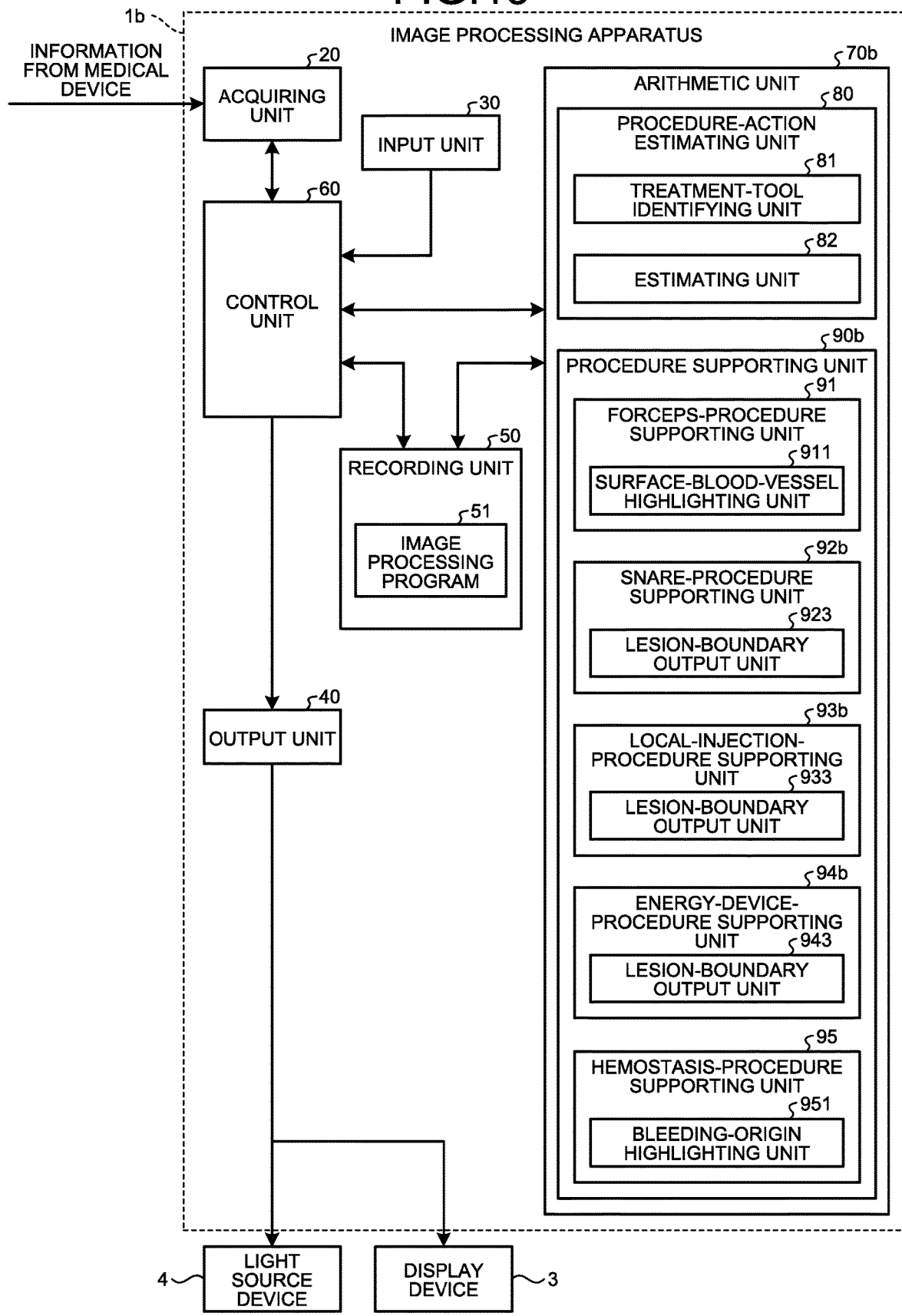
FIG. 19 is a block diagram illustrating a configuration of an image processing apparatus according to a third embodiment of the disclosure.

FIG. 19 is a block diagram illustrating a configuration of an image processing apparatus according to the third embodiment of the disclosure. An image processing apparatus 1*b* illustrated in FIG. 19 includes an arithmetic unit 70*b* in place of the arithmetic unit 70 in the image processing apparatus 1 according to the first embodiment described above.

Detailed Configuration of Arithmetic Unit

The arithmetic unit 70*b* includes a procedure supporting unit 90*b* in place of the procedure supporting unit 90 according to the first embodiment described above. The procedure supporting unit 90*b* supports a procedure by an operator according to an estimation result by the procedure-action estimating unit 80. The procedure supporting unit 90*b* includes a snare-procedure supporting unit 92*b*, a local-injection procedure supporting unit 93*b*, and an energy-device-procedure supporting unit 94*b* in place of the snare-procedure supporting unit 92, the local-injection procedure supporting unit 93, and the energy-device-procedure supporting unit 94 according to the first embodiment described above.

The snare-procedure supporting unit 92*b* performs, when the estimating unit 82 estimates as a snare procedure, a support according to a procedure with a snare. The snare-procedure supporting unit 92*b* includes a lesion-boundary output unit 923 that identifies a lesion region, and outputs a boundary of this lesion region.

The local-injection procedure supporting unit 93*b* performs, when the estimating unit 82 estimates as a local injection procedure, a support according to a local injection procedure. The local-injection procedure supporting unit 93*b* includes a lesion-boundary output unit 933 that identifies a lesion region, and outputs a boundary of this lesion region.

The energy-device-procedure supporting unit 94*b* performs, when the estimating unit 82 estimates as an energy device procedure, a support according to a procedure with an energy device. The energy-device-procedure supporting unit 94*b* includes a lesion-boundary output unit 943 that identifies a lesion region, and outputs a boundary of this lesion region.

Processing of Image Processing Apparatus

Next, processing performed by the image processing apparatus 1*b* will be described. The image processing apparatus 1*b* performs processing similar to that of the image processing apparatus 1 according to the first embodiment described above, but differs in each of the snare-procedure support processing in FIG. 6, the local-injection-procedure support processing in FIG. 7, and the high-frequency-knife-procedure support processing in FIG. 8 described above. Hereinafter, the snare-procedure support processing, the local-injection-procedure support processing, and the high-frequency-knife-procedure support processing, performed by the image processing apparatus 1*b* will be described.

Snare-Procedure Support Processing

Figure 20:
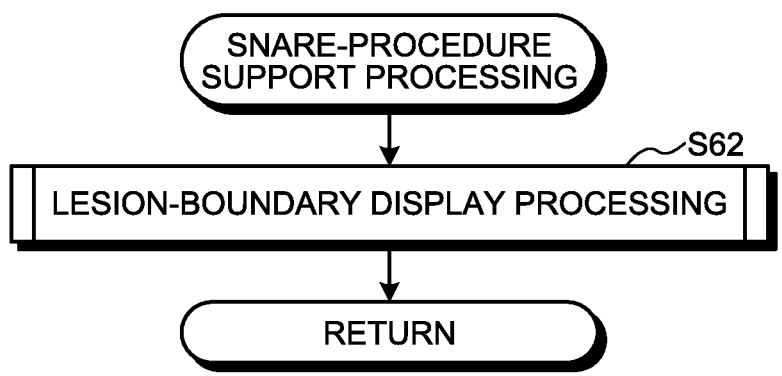
FIG. 20 is a flowchart illustrating an overview of snare-procedure support processing performed by a snare-procedure supporting unit according to the third embodiment of the disclosure.

First the snare-procedure support processing performed by the image processing apparatus 1*b* will be described. FIG. 20 is a flowchart illustrating an overview of the snare-procedure support processing performed by the snare-procedure supporting unit 92*b*.

As illustrated in FIG. 20, the snare-procedure supporting unit 92*b* performs lesion-region-boundary display processing of identifying a lesion region in an endoscopic image, and outputting a boundary of this lesion region to the display device 3 (step S62). After step S62, the image processing apparatus 1*b* returns to the main routine in FIG. 3.

Lesion-Region Display Processing

Figure 21:
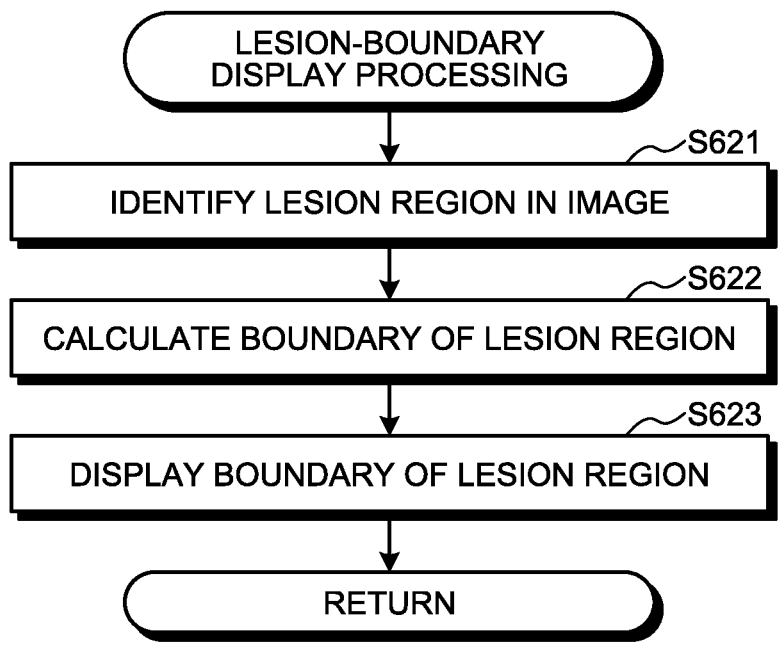
FIG. 21 is a flowchart illustrating an overview of lesion-boundary display processing in FIG. 20.

FIG. 21 is a flowchart illustrating an overview of the lesion-boundary display processing at step S62 in FIG. 20. As illustrated in FIG. 21, the lesion-boundary output unit 923 identifies a lesion region in an endoscopic image (step S621). Specifically, the lesion-boundary output unit 923 extracts a region of a polyp from the endoscopic image by using a publicly-known polyp-candidate detection processing (for example, refer to JP-A-2007-244518), and identifies this extracted region as a lesion region. Moreover, the lesion-boundary output unit 923 may be configured to increase extraction accuracy of a lesion region appearing in an endoscopic image by using a publicly-known snakes (reference: *DIGITAL IMAGE PROCESSING* [revised new version], CG-ARTS society: p. 210, Region Separation Processing Using Edges Between Subject and Background) or graph cut (reference: *DIGITAL IMAGE PROCESSING* [revised new version], CG-ARTS society: p. 212, Region Separation Processing Using Graph Cut).

Subsequently, the lesion-boundary output unit 923 calculates a boundary of the lesion region for the lesion region identified at step S621 described above (step S622). Specifically, the lesion-boundary output unit 923 subjects the lesion region identified at step S621 described above to threshold processing, or the like to convert into a binary mask image, and to publicly-known edge extraction (reference: *DIGITAL IMAGE PROCESSING* [revised new version], CG-ARTS society: p. 105, Edge Extraction) to extract an edge of the binary mask image, thereby calculating a boundary of the lesion region.

Thereafter, the lesion-boundary output unit 923 outputs the boundary of the lesion region calculated at step S622 to the display device 3 (step S623). In this case, the lesion-boundary output unit 933 superimposes the boundary of the lesion region on the endoscopic image, to output to the display device 3. After step S623, the image processing apparatus 1*b* returns to the subroutine in FIG. 20.

Local-Injection-Procedure Support Processing

Figure 22:
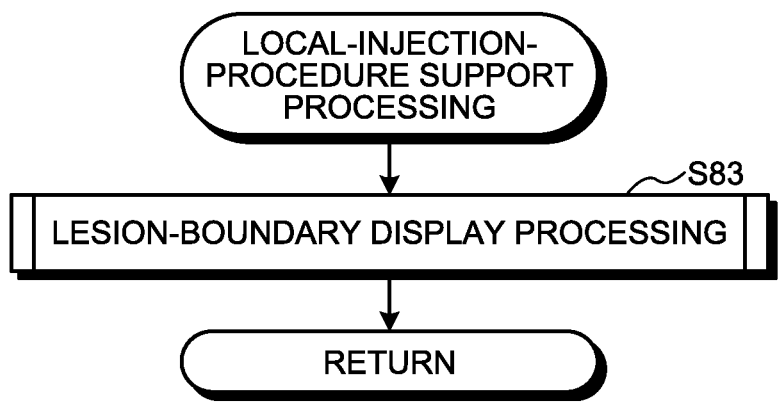
FIG. 22 is a flowchart illustrating an overview of local-injection-procedure support processing performed by a local-injection procedure supporting unit according to the third embodiment of the disclosure.

Next, the local-injection-procedure support processing performed by the local-injection procedure supporting unit 93*b* will be described. FIG. 22 is a flowchart illustrating an overview of the local-injection-procedure support processing performed by the local-injection procedure supporting unit 93b.

As illustrated in FIG. 22, the local-injection procedure supporting unit 93b performs lesion-region-boundary display processing of identifying a lesion region in an endoscopic image, and outputting a boundary of this lesion region to the display device 3 (step S83). Specifically, the lesion-boundary output unit 933 performs processing similar to the lesion-boundary display processing in FIG. 21 described above. After step S83, the image processing apparatus 1b returns to the main routine in FIG. 3.

High-Frequency-Knife-Procedure Support Processing

Figure 23:
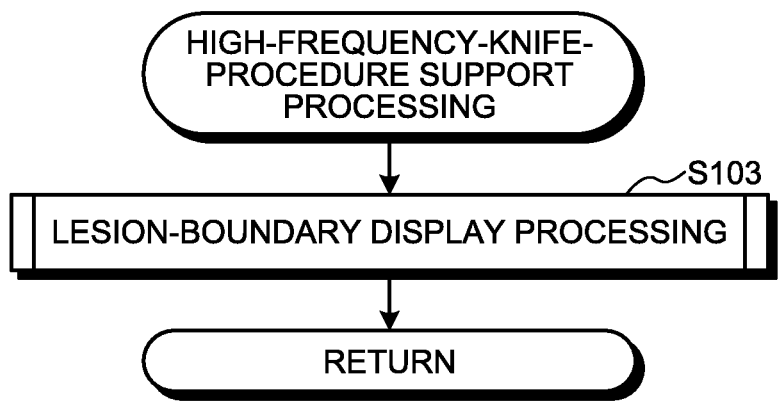
FIG. 23 is a flowchart illustrating an overview of high-frequency-knife-procedure support processing performed by an energy-device-procedure supporting unit according to the third embodiment of the disclosure.

Next, the high-frequency-knife-procedure processing performed by the energy-device-procedure supporting unit 94b will be described. FIG. 23 is a flowchart illustrating an overview of the high-frequency-knife-procedure support processing performed by the energy-device-procedure supporting unit 94b.

As illustrated in FIG. 23, the energy-device-procedure supporting unit 94b performs the lesion-region-boundary display processing of identifying a lesion region in an endoscopic image, and outputting a boundary of this lesion region to the display device 3 (step S103). Specifically, the lesion-boundary output unit 943 performs processing similar to the lesion-boundary display processing in FIG. 21 described above. After step S103, the image processing apparatus 1b returns to the main routine in FIG. 3.

According to the third embodiment of the disclosure described above, a boundary of a lesion region is output and, therefore, it is possible to prevent the lesion from being left without being removed by a treatment tool.

Fourth Embodiment

Next, a fourth embodiment of the disclosure will be described. An image processing apparatus according to the fourth embodiment differs in a configuration from the arithmetic unit 70 in the image processing apparatus 1 according to the first embodiment described above. Hereinafter, a configuration of the image processing apparatus according to the fourth embodiment will be described, and then processing performed by the image processing apparatus according to the fourth embodiment will be described. Note that the same reference symbols are assigned to the same components as the image processing apparatus 1 according to the first embodiment described above, and description thereof is omitted.

Configuration of Image Processing Apparatus

Figure 24:
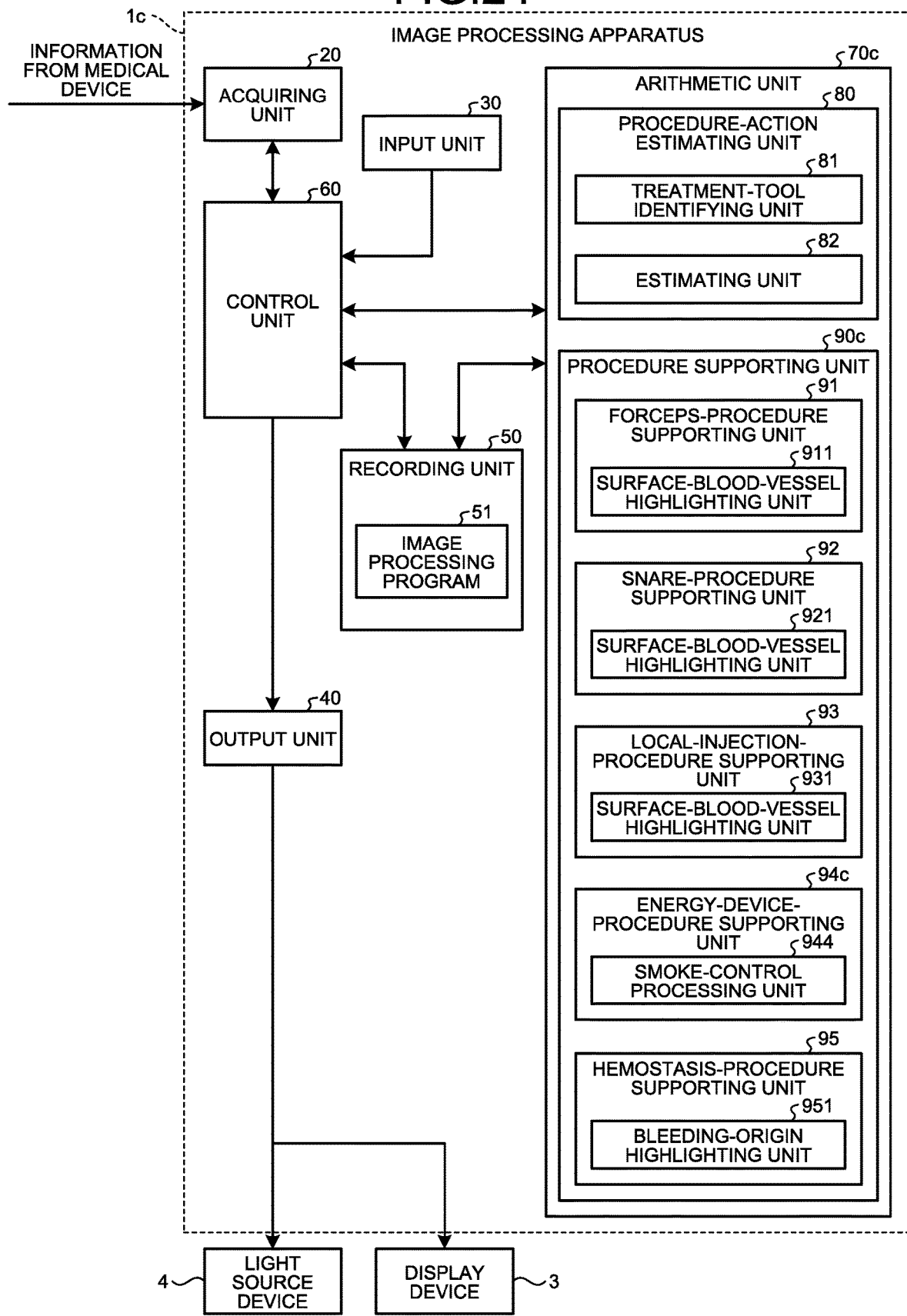
FIG. 24 is a block diagram illustrating a configuration of an image processing apparatus according to a fourth embodiment of the disclosure.

FIG. 24 is a block diagram illustrating a configuration of an image processing apparatus according to the fourth embodiment of the disclosure. An image processing apparatus 1c illustrated in FIG. 24 includes an arithmetic unit 70c in place of the arithmetic unit 70 of in the image processing apparatus 1 according to the first embodiment described above.

Detailed Configuration of Arithmetic Unit

The arithmetic unit 70c includes a procedure supporting unit 90c in place of the procedure supporting unit 90 according to the first embodiment described above. The procedure supporting unit 90c supports a procedure by an operator according to an estimation result by the procedure-action estimating unit 80. The procedure supporting unit 90c includes an energy-device-procedure supporting unit 94c in place of the energy-device-procedure supporting unit 94 according to the first embodiment described above.

The energy-device-procedure supporting unit 94c performs, when the estimating unit 82 estimates as an energy device procedure, a support according to a procedure with an energy device. The energy-device-procedure supporting unit 94c includes a smoke-control processing unit 944 that subjects an endoscopic image to image processing of suppressing smoke generated at a procedure, to output to the display device 3.

Processing of Image Processing Apparatus

Next, processing performed by the image processing apparatus 1c will be described. The image processing apparatus 1c performs processing similar to that of the image processing apparatus 1 according to the first embodiment described above, but differs in the energy-device-procedure support processing in FIG. 8 described above. Hereinafter, the energy-device-procedure support processing performed by the image processing apparatus 1c will be described.

High-Frequency-Knife-Procedure Support Processing

Figure 25:
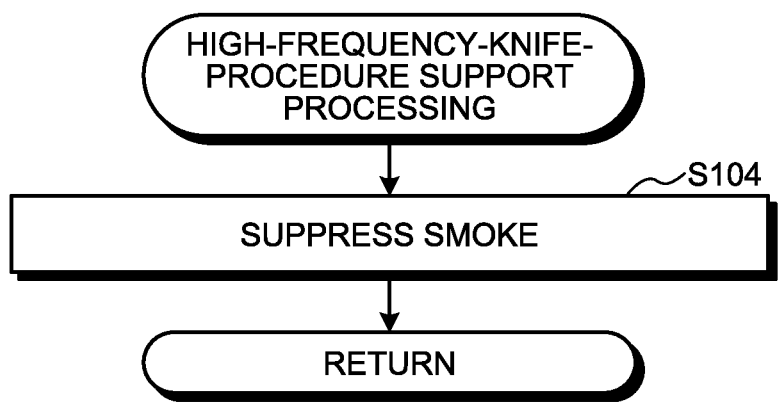
FIG. 25 is a flowchart illustrating an overview of high-frequency-knife-procedure support processing performed by an energy-device-procedure supporting unit according to the fourth embodiment of the disclosure.

FIG. 25 is a flowchart illustrating an overview of high-frequency-knife-procedure support processing performed by the energy-device-procedure supporting unit 94c.

As illustrated in FIG. 25, the energy-device-procedure supporting unit 94c performs the processing of suppressing smoke generated when a procedure is performed by using a high frequency knife (step S104). Specifically, the smoke-control processing unit 944 generates an endoscopic image subjected to image processing of suppressing smoke generated at resection processing of a living tissue by an energy device or haze caused by the smoke by a technique, such as a publicly-known dehaze processing and super resolution processing, to output to the display device 3. After step S104, the image processing apparatus 1c returns to the main routine in FIG. 3.

According to the fourth embodiment of the disclosure described above, it is possible to suppress smoke generated when a procedure is performed by using an energy device.

Fifth Embodiment

Next, a fifth embodiment of the disclosure will be described. An image processing apparatus according to the fifth embodiment differs in a configuration from the arithmetic unit 70 of the image processing apparatus 1 according to the first embodiment described above. Hereinafter, a configuration of the image processing apparatus according to the fifth embodiment will be described, and then processing performed by the image processing apparatus according to the fifth embodiment will be described. Note that the same reference symbols are assigned to the same components as the image processing apparatus 1 according to the first embodiment described above, and description thereof is omitted.

Configuration of Image Processing Apparatus

Figure 26:
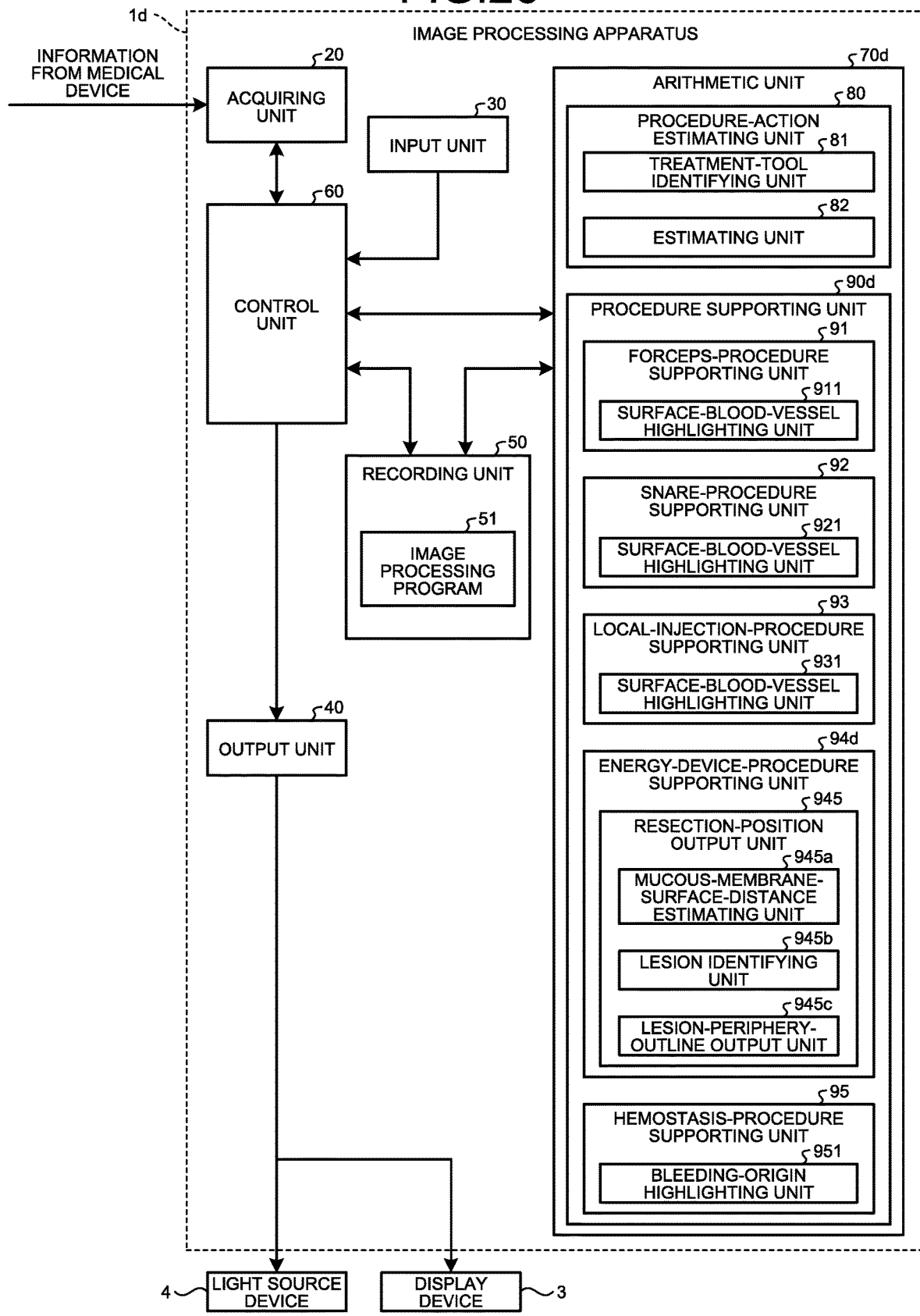
FIG. 26 is a block diagram illustrating a configuration of an image processing apparatus according to a fifth embodiment of the disclosure.

FIG. 26 is a block diagram illustrating a configuration of an image processing apparatus according to the fifth embodiment of the disclosure. An image processing apparatus 1d illustrated in FIG. 26 includes an arithmetic unit 70d in place of the arithmetic unit 70 in the image processing apparatus 1 according to the first embodiment described above.

Detailed Configuration of Arithmetic Unit

The arithmetic unit 70d includes a procedure supporting unit 90d in place of the procedure supporting unit 90 according to the first embodiment described above. The procedure supporting unit 90d supports a procedure by an operator according to an estimation result by the procedure-action estimating unit 80. The procedure supporting unit 90d includes an energy-device-procedure supporting unit 94d in place of the energy-device-procedure supporting unit 94 according to the first embodiment described above.

The energy-device-procedure supporting unit 94d performs, when the estimating unit 82 estimates as an energy device procedure, a support according to a procedure with an energy device. The energy-device-procedure supporting unit 94d includes a resection-position output unit 945 that outputs a resection position by an energy device. Moreover, the resection-position output unit 945 includes a mucous-membrane-surface-distance estimating unit 945a that estimates an imaging distance at respective pixel coordinates in an endoscopic image, a lesion identifying unit 945b that identifies a lesion region, and a lesion-periphery-outline output unit 945c that outputs an outline of a peripheral region of a lesion on a mucous membrane to the display device 3.

Processing of Image Processing Apparatus

Next, processing performed by the image processing apparatus 1d will be described. The image processing apparatus 1d performs processing similar to that of the image processing apparatus 1 according to the first embodiment described above, but differs in the energy-device-procedure support processing in FIG. 8 described above. Hereinafter, the energy-device-procedure support processing performed by the image processing apparatus 1d will be described.

High-Frequency-Knife-Procedure Support Processing

Figure 27:
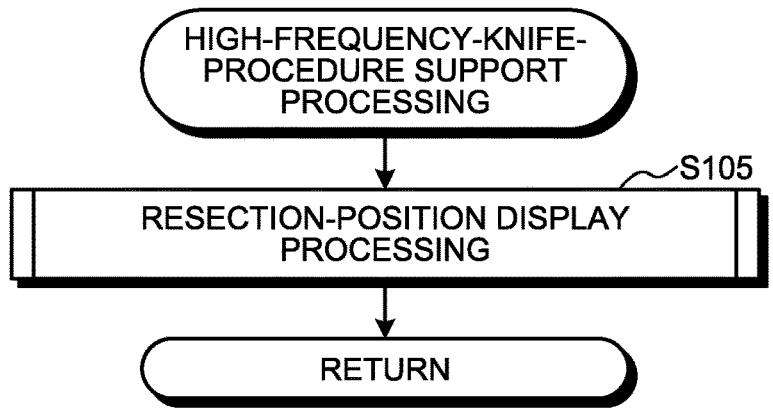
FIG. 27 is a flowchart illustrating an overview of high-frequency-knife-procedure support processing performed by an energy-device-procedure supporting unit according to the fifth embodiment of the disclosure.

FIG. 27 is a flowchart illustrating an overview of high-frequency-knife-procedure support processing performed by the energy-device-procedure supporting unit 94d.

As illustrated in FIG. 27, the resection-position output unit 945 performs resection-position display processing of displaying a resection position by an energy device on the display device 3 (step S105). After step S105, the image processing apparatus 1d returns to the main routine in FIG. 3.

Resection-Position Display Processing

Figure 28:
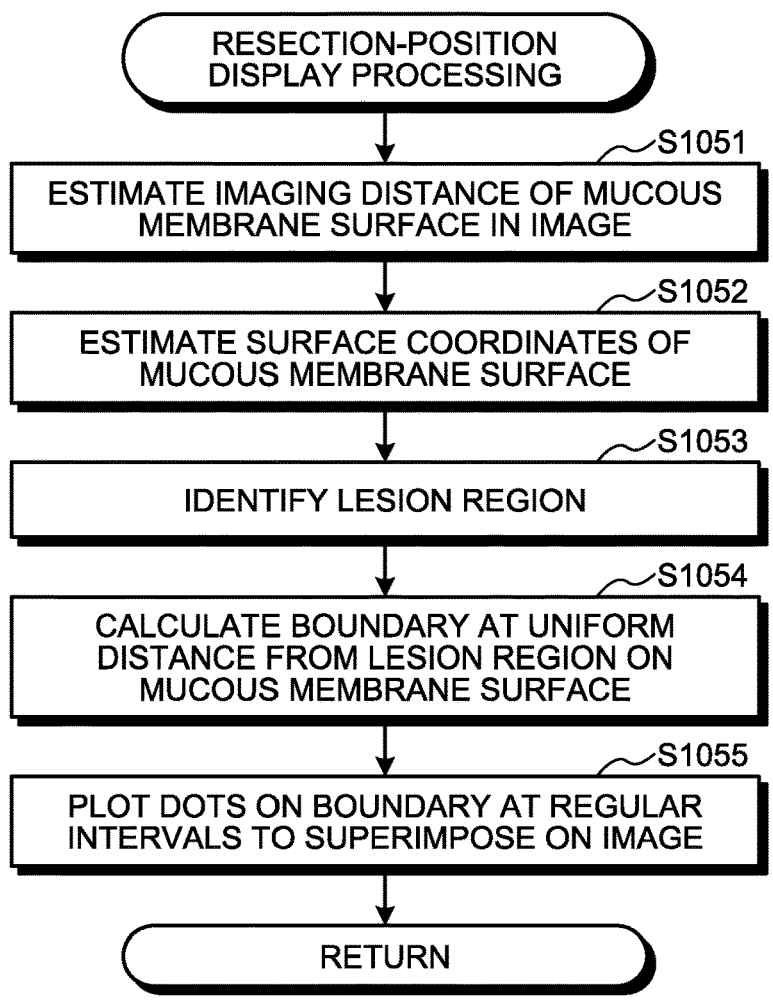
FIG. 28 is a flowchart illustrating an overview of resection-position display processing in FIG. 27.

FIG. 28 is a flowchart illustrating an overview of the resection-position display processing at step S105 in FIG. 27. As illustrated in FIG. 28, first, the mucous-membrane-surface-distance estimating unit 945a estimates an imaging distance at respective pixel coordinates in an endoscopic image (step S1051). Specifically, the mucous-membrane-surface-distance estimating unit 945a estimates an imaging distance at respective pixel coordinates in the endoscopic image by a method similar to that in FIG. 14 described above.

Subsequently, the mucous-membrane-surface-distance estimating unit 945a estimates surface coordinates of a mucous membrane surface appearing at respective pixels of the endoscopic image (step S1052). Specifically, the mucous-membrane-surface-distance estimating unit 945a estimates surface coordinates of a mucous membrane surface appearing at respective pixels in the endoscopic image by a method similar to that of the forceps-arrival-point estimating unit 912b described above and, thus, detailed explanation is omitted.

Thereafter, the lesion identifying unit 945b identifies a lesion region in the endoscopic image (step S1053). Specifically, the lesion identifying unit 945b identifies a lesion region in the endoscopic image by a method at step S621 in FIG. 21 described above.

Subsequently, the lesion-periphery-outline output unit 945c calculates a boundary of the lesion region for the lesion region identified at step S1053 described above. (step S1054). Specifically, the lesion-periphery-outline output unit 945c identifies surface coordinates of a lesion boundary based on a lesion boundary calculated by the method at step S622 in FIG. 21 described above, and on the surface coordinates of the mucous membrane surface estimated at step S1052 described above. The lesion-periphery-outline output unit 945c then calculates a surface coordinate group having a uniform distance from the lesion boundary on the surface coordinates, and determines a value acquired as a result of this calculation as a boundary. Furthermore, the lesion-periphery-outline output unit 945c performs conversion from the surface coordinates to coordinates in the endoscopic image by using Equations (5) and (6) below.

$$x_j = f \frac{X_i}{Z_i} \quad (5)$$

$$y_j = f \frac{Y_i}{Z_i} \quad (6)$$

Figure 29:
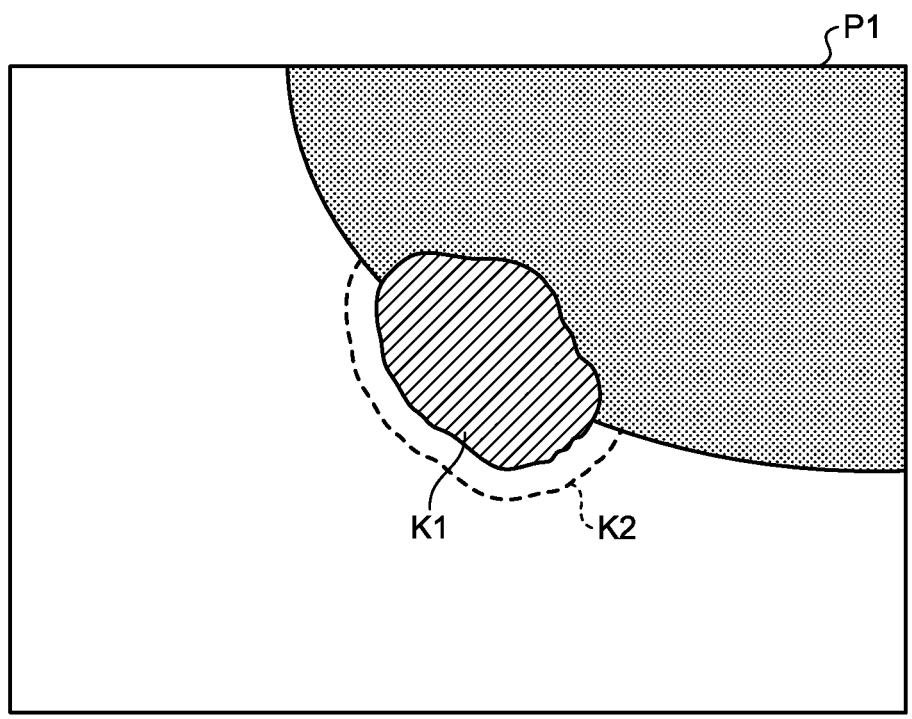
FIG. 29 illustrates an example of an image in which a resection position is superimposed on an endoscopic image.

Thereafter, the lesion-periphery-outline output unit 945c outputs an endoscopic image in which dots are plotted at regular intervals on the boundary of the lesion region appearing in the endoscopic image, to the display device 3 (step S1055). Specifically, the lesion-periphery-outline output unit 945c counts pixel values clockwise or counterclockwise on the boundary, starting from one point on the boundary calculated at step S1054 described above (an end point when the boundary is an opening curve) as a starting point. The lesion-periphery-outline output unit 945c records as dots to be plotted when the pixel values reach a certain number, and resets the counter back to 0. The lesion-periphery-outline output unit 945c finishes recording of plots, and superimposes a mark K2 of a circle or the like on the recorded plots on the endoscopic image, to output to the display device 3. For example, as illustrated in FIG. 29, the lesion-periphery-outline output unit 945c superimposes the mark K2 on the endoscopic image P1 around a lesion region K1, to output to the display device 3. After step S105, the image processing apparatus 1d returns to the subroutine in FIG. 27.

According to the fifth embodiment of the disclosure described above, a resection position is displayed and, therefore, resection can be performed easily.

Sixth Embodiment

Next, a sixth embodiment of the disclosure will be described. An image processing apparatus according to the sixth embodiment differs in a configuration from the arithmetic unit 70 of the image processing apparatus 1 according to the first embodiment described above. Hereinafter, a configuration of the image processing apparatus according to the sixth embodiment will be described, and then processing performed by the image processing apparatus according to the sixth embodiment will be described. Note that the same reference symbols are assigned to the same components as the image processing apparatus 1 according to the first embodiment described above, and description thereof is omitted.

Configuration of Image Processing Apparatus

Figure 30:
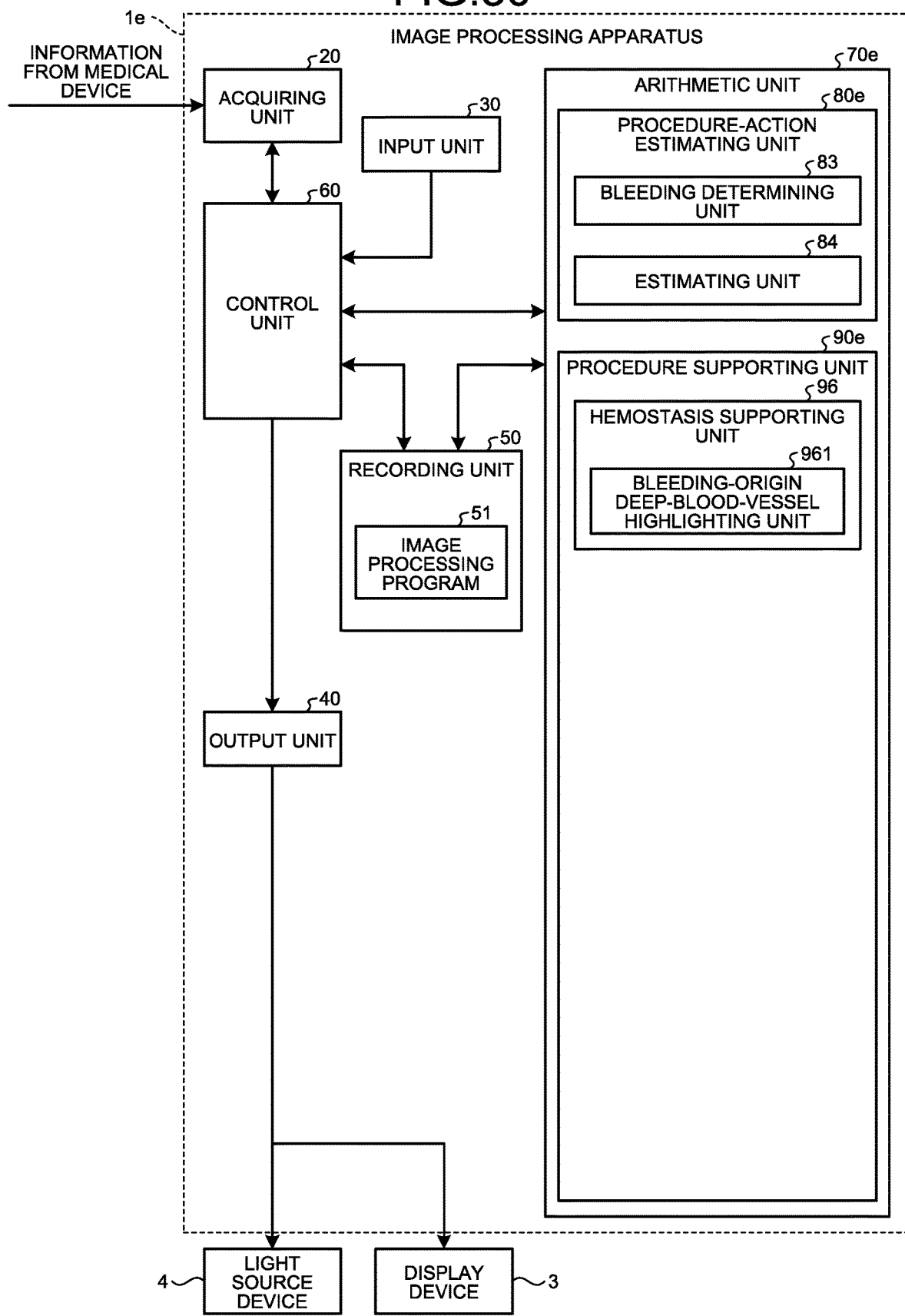
FIG. 30 is a block diagram illustrating a configuration of an image processing apparatus according to a sixth embodiment of the disclosure.

FIG. 30 is a block diagram illustrating a configuration of an image processing apparatus according to the sixth embodiment of the disclosure. An image processing apparatus 1e illustrated in FIG. 30 includes an arithmetic unit 70e in place of the arithmetic unit 70 in the image processing apparatus 1 according to the first embodiment described above.

Detailed Configuration of Arithmetic Unit

The arithmetic unit 70e includes a procedure-action estimating unit 80e and a procedure supporting unit 90e in place of the procedure supporting unit 90 according to the first embodiment described above.

The procedure-action estimating unit 80e includes a bleeding determining unit 83 that determines bleeding, and an estimating unit 84 that estimates an action.

The procedure supporting unit 90e includes a hemostasis supporting unit 96 that performs a support at the time of hemostasis procedure. The hemostasis supporting unit 96 includes a bleeding-origin deep-blood-vessel highlighting unit 961 that highlights a bleeding origin or a deep blood vessel when the estimating unit 84 estimates as hemostasis procedure.

Processing of Image Processing Apparatus

Figure 31:
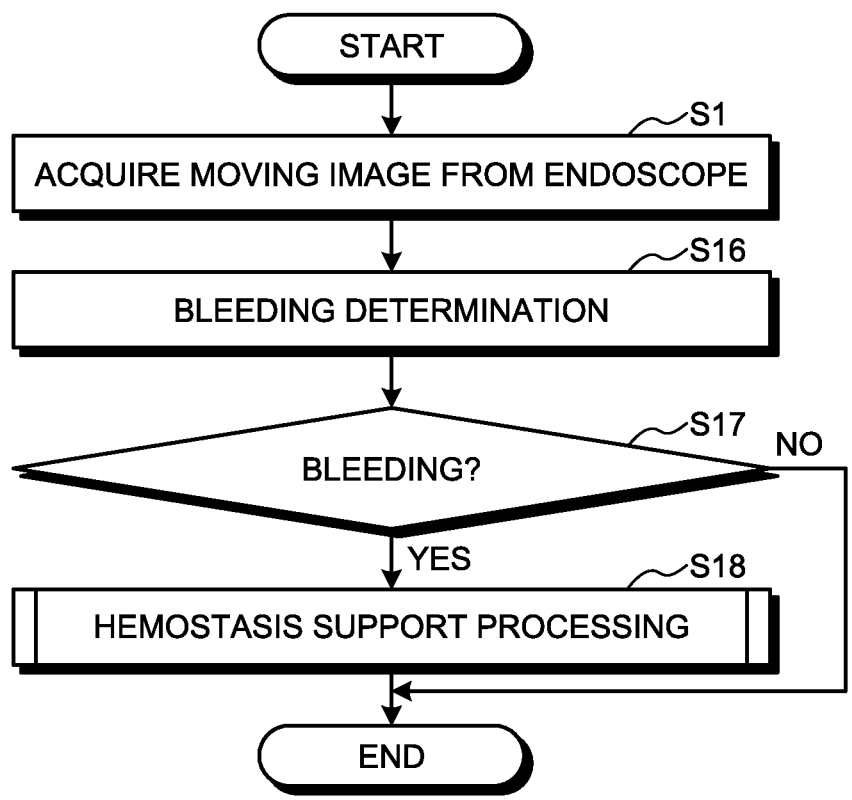
FIG. 31 is a flowchart illustrating an overview of processing performed by the image processing apparatus according to the sixth embodiment of the disclosure.

Next, processing performed by the image processing apparatus 1e will be described. FIG. 31 is a flowchart illustrating an overview of processing performed by the image processing apparatus 1e. As illustrated in FIG. 31, the image processing apparatus 1e performs step S16 to step S18 instead of step S2 to step S15 in FIG. 3. In the following, step S16 to step S18 will be described.

At step S16, the bleeding determining unit 83 determines whether bleeding is included in an endoscopic image. Specifically, the bleeding determining unit 83 determines that bleeding is included in the endoscopic image when the number of pixels of red in the endoscopic image is equal to or larger than a threshold. Note that the bleeding determining unit 83 may determine whether bleeding is included in an endoscopic image by bleeding-edge detection processing (for example, JP-A-2006-304995).

At step S17, when the estimating unit 84 estimates that bleeding is included in an endoscopic image based on a determination result of the bleeding determining unit 83 (step S17: YES), the hemostasis supporting unit 96 performs hemostasis support processing (step S18). After step S18, the image processing apparatus 1e ends this processing. On the other hand, when the estimating unit 82 estimates that bleeding is not included in an endoscopic image based on a determination result of the bleeding determining unit 83 (step S17: NO), the image processing apparatus 1e ends this processing.

Hemostasis Support Processing

Figure 32:
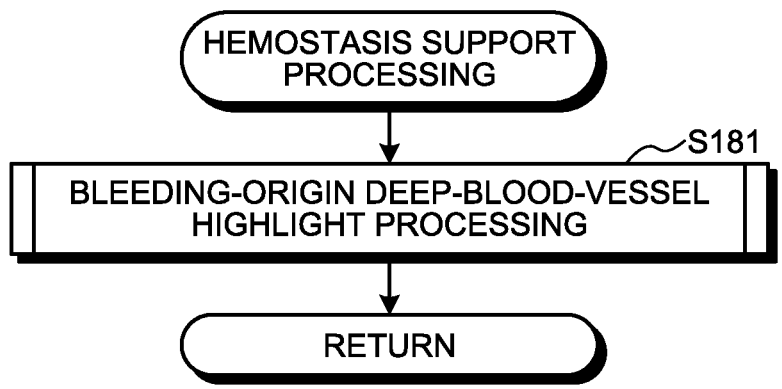
FIG. 32 is a flowchart illustrating an overview of hemostasis support processing in FIG. 31.

FIG. 32 is a flowchart illustrating an overview of the hemostasis support processing at step S18 in FIG. 31. As illustrated in FIG. 32, the bleeding-origin deep-blood-vessel highlighting unit 961 performs processing of highlighting a bleeding origin or a deep blood vessel (step S181). Specifically, the bleeding-origin deep-blood-vessel highlighting unit 961 performs processing similar to that at step S101 in FIG. 8 described above. After step S181, the image processing apparatus 1e returns to the main routine in FIG. 31.

According to the sixth embodiment of the disclosure described above, a bleeding origin or a deep blood vessel is highlighted and, therefore, hemostasis procedure can be performed easily.

Modification of Sixth Embodiment

Next, a modification of the sixth embodiment of the disclosure will be described. The modification of the sixth embodiment differs from the hemostasis support processing performed by the bleeding-origin deep-blood-vessel highlighting unit 961. Hereinafter, the hemostasis support processing performed by the bleeding-origin deep-blood-vessel highlighting unit 961 according to the modification of the sixth embodiment will be described. Note that the same reference symbols are assigned to the same components as the image processing apparatus 1e according to the sixth embodiment described above, and description thereof is omitted.

Hemostasis Support Processing

Figure 33:
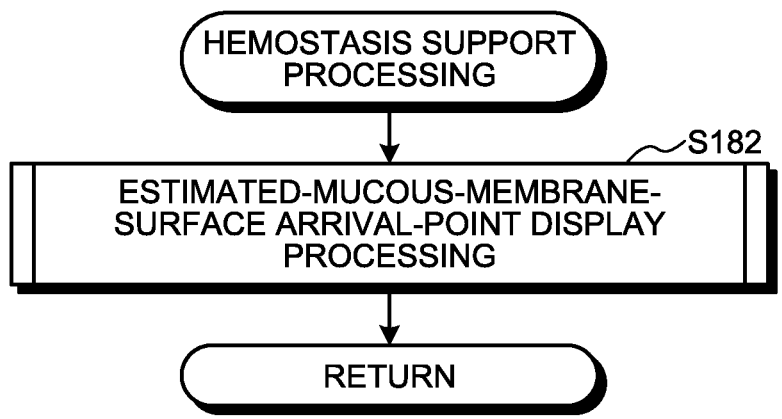
FIG. 33 is a flowchart illustrating an overview of the hemostasis support processing performed by a bleeding-origin deep-blood-vessel highlighting unit according to a modification of the sixth embodiment of the disclosure.

FIG. 33 is a flowchart illustrating an overview of the hemostasis support processing performed by the bleeding-origin deep-blood-vessel highlighting unit 961 according to the modification of the sixth embodiment of the disclosure. As illustrated in FIG. 33, the bleeding-origin deep-blood-vessel highlighting unit 961 performs estimated-mucous-membrane-surface arrival-point display processing (step S182). Specifically, the bleeding-origin deep-blood-vessel highlighting unit 961 performs processing similar to the estimated-mucous-membrane-surface arrival-point display processing in FIG. 13 described above. After step S182, the image processing apparatus 1e returns to the main routine in FIG. 30.

According to the modification of the sixth embodiment of the disclosure described above, an estimated point of a treatment tool at which a hemostasis device reaches a mucous membrane surface at the time of bleeding is displayed and, therefore, a speedy support can be provided to an operator.

Other Embodiments

The disclosure can be implemented by executing an image processing program recorded in a recording device by a computer system, such as a personal computer and a workstation. Moreover, such a computer system may be connected to a device, such as another computer system and a server, through a local area network (LAN), a wide area network (WAN), or a public line, such as the Internet, to be used. In this case, the image processing apparatus of the first to sixth embodiments and modifications thereof may be configured to acquire image data of a intraluminal image through these networks, to output an image processing result to various kinds of output devices, such as a viewer and a printer, connected to these networks, or to store an image processing result in a storage device connected through these networks, for example, a recording medium readable by a reader device connected to a network, and the like.

The sequence of processing among steps has been indicated by using expressions, "first", "thereafter", "subsequently", and the like in explanation of the flowcharts in the present application, but it is noted that the order of processing necessary to implement the disclosure is not uniquely determined by those expressions. That is, the order of processing in flowcharts described in the present application can be changed within a range not causing contradictions.

According to the disclosure, an effect that a support according to a procedure in endoscopy performed by an operator can be provided is produced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor including hardware, the processor being configured to:
estimate, based on image information from a medical device that includes at least an endoscope, a plurality of procedure actions of an operator of the endoscope,
wherein the image information includes an image signal that is imaged by the endoscope, and
wherein estimating the plurality of procedure actions of the operator of the endoscope comprises:
identify, by image recognition using a template image, forceps as a kind of treatment tool appearing in an endoscopic image corresponding to the image signal; and
estimate an action of the operator as a forceps procedure when the kind of the treatment tool is identified as the forceps;
perform a support according to a procedure with the forceps when the action of the operator is estimated as the forceps procedure, wherein performing the support comprises estimate an imaging distance at respective pixel coordinates in the endoscopic image; and
output a display for performing the support to a display.

2. The image processing apparatus according to claim 1, wherein in performing the support, the processor is configured to highlight a surface blood vessel as the support.

3. The image processing apparatus according to claim 1, wherein in performing the support, the processor is further configured to estimate an arrival point at which the forceps reach a mucous membrane surface, based on a positional relationship between an optical center of the endoscope and a forceps inlet, and on the imaging distance.

4. The image processing apparatus according to claim 3, wherein the processor is configured to output the estimated arrival point to the display.

5. An image processing apparatus comprising:
a processor including hardware, the processor being configured to:
estimate, based on image information from a medical device that includes at least an endoscope, a plurality of procedure actions of an operator of the endoscope,
wherein the image information includes an image signal that is imaged by the endoscope, and
wherein estimating the plurality of procedure actions of the operator of the endoscope comprises:
identify, by image recognition using a template image, a snare as a kind of treatment tool appearing in an endoscopic image corresponding to the image signal; and
estimate an action of the operator as a snare procedure when the kind of the treatment tool is identified as the snare;
perform a support according to a procedure with the snare when the action of the operator is estimated as the snare procedure, wherein performing the support comprises estimate an imaging distance at respective pixel coordinates in the endoscopic image; and
output a display for performing the support to a display.

6. The image processing apparatus according to claim 5, wherein in performing the support, the processor is configured to highlight a surface blood vessel as the support.

7. The image processing apparatus according to claim 5, wherein the processor is configured to identify a lesion region, and output a boundary of the lesion region as the support.

8. The image processing apparatus according to claim 7, wherein the processor is configured to generate an image including the boundary of the lesion region, the boundary being marked by plots.

9. The image processing apparatus according to claim 5, wherein in performing the support, the processor is further configured to estimate an arrival point at which the snare reaches a mucous membrane surface, based on a positional relationship between an optical center of the endoscope and a treatment tool channel inlet, and on the imaging distance.

10. An image processing apparatus comprising:
a processor including hardware, the processor being configured to:
estimate, based on image information from a medical device that includes at least an endoscope, a plurality of procedure actions of an operator of the endoscope,
wherein the image information includes an image signal that is imaged by the endoscope, and
wherein estimating the plurality of procedure actions of the operator of the endoscope comprises:
identify, by image recognition using a template image, an injection needle as a kind of treatment tool appearing in an endoscopic image corresponding to the image signal; and
estimate an action of the operator as a local injection procedure when the kind of the treatment tool is identified as the injection needle;
perform a support according to a procedure with the injection needle when the action of the operator is estimated as the local injection procedure, wherein the support comprises:
highlight a surface blood vessel;
identify a lesion region and output a boundary of the lesion region;
estimate an imaging distance at respective pixel coordinates in the endoscopic image; and
estimate an arrival point at which the injection needle reaches a mucous membrane surface, based on a positional relationship between an optical center of the endoscope and a treatment tool channel inlet, and on the imaging distance; and
output the estimated arrival point to a display.

11. An image processing apparatus comprising:
a processor including hardware, the processor being configured to:
estimate, based on image information from a medical device that includes at least an endoscope, a plurality of procedure actions of an operator of the endoscope,
wherein the image information includes an image signal that is imaged by the endoscope, and
wherein estimating the plurality of procedure actions of the operator of the endoscope comprises:
identify, by image recognition using a template image, an energy device as a kind of treatment tool appearing in an endoscopic image corresponding to the image signal; and
estimate an action of the operator as an energy device procedure when the kind of the treatment tool is identified as the energy device;

perform a support according to a procedure with the energy device when the action of the operator is estimated as the energy device procedure, wherein performing the support comprises estimate an imaging distance at respective pixel coordinates in the endoscopic image; and output a display for performing the support to a display.

12. The image processing apparatus according to claim 11, wherein in performing the support, the processor is configured to highlight a deep blood vessel as the support.

13. The image processing apparatus according to claim 11, wherein the processor is configured to identify a lesion region, and output a boundary of the lesion region as the support.

14. The image processing apparatus according to claim 13, wherein the processor is configured to generate an image including the boundary of the lesion region, the boundary being marked by plots.

15. The image processing apparatus according to claim 11, wherein the processor is configured to subject the endoscopic image to image processing of suppressing smoke generated at a procedure by the energy device.

16. The image processing apparatus according to claim 15, wherein the processor is configured to output the endoscopic image subjected to image processing of suppressing smoke generated at the procedure of the energy device to the display.

17. The image processing apparatus according to claim 11, wherein in performing the support, the processor is further configured to estimate an arrival point at which the energy device reaches a mucous membrane surface, based on a positional relationship between an optical center of the endoscope and a forceps inlet, and on the imaging distance.

18. The image processing apparatus according to claim 17, wherein the processor is configured to output the estimated arrival point to the display.

* * * * *